(12) United States Patent
Baer et al.

(10) Patent No.: US 6,184,973 B1
(45) Date of Patent: *Feb. 6, 2001

(54) LASER CAPTURE MICRODISSECTION PRESSURE PLATE AND TRANSFER ARM

(75) Inventors: Thomas M. Baer, Mountain View; Mark A. Enright, Cupertino; David F. Head, Los Gatos; Christopher E. Todd, San Jose, all of CA (US)

(73) Assignee: Arcturus Engineering, Inc., Mountain View, CA (US)

( * ) Notice: Under 35 U.S.C. 154(b), the term of this patent shall be extended for 0 days.

This patent is subject to a terminal disclaimer.

(21) Appl. No.: 09/058,711

(22) Filed: Apr. 10, 1998

Related U.S. Application Data

(63) Continuation of application No. 09/018,452, filed on Feb. 4, 1998.
(60) Provisional application No. 60/060,731, filed on Oct. 1, 1997, and provisional application No. 60/037,864, filed on Feb. 7, 1997, now abandoned.

(51) Int. Cl.$^7$ .................................................. G01N 1/00
(52) U.S. Cl. ............................................................ 356/36
(58) Field of Search .................................. 356/244–246, 356/237, 369, 36; 428/328, 447, 452, 332, 339; 422/102, 55–58, 61; 250/559.42, 559.48; 359/385, 393, 391, 398

(56) References Cited

U.S. PATENT DOCUMENTS

| | | | |
|---|---|---|---|
| 3,680,947 | 8/1972 | Wanesky | 350/81 |
| 3,705,769 | 12/1972 | Johannsmeier | 355/91 |

(List continued on next page.)

FOREIGN PATENT DOCUMENTS

| | | | |
|---|---|---|---|
| 196 03 996 A1 | 8/1997 | (DE) | G01N/1/04 |
| WO91/07683 | 5/1991 | (WO) | G02B/21/26 |

(List continued on next page.)

OTHER PUBLICATIONS

Emmert–Buck, M. et al., "Laser Capture Microdissection", *Science*, vol. 274, Nov. 8, 1996, pp. 998–1001.

(List continued on next page.)

*Primary Examiner*—Frank G. Font
*Assistant Examiner*—Tu T. Nguyen
(74) *Attorney, Agent, or Firm*—Wilson, Sonsini, Goodrich & Rosati

(57) ABSTRACT

Systems and methods for laser capture microdissection are disclosed. A laser capture microdissection method includes: providing a sample that is to undergo laser capture microdissection; positioning the sample within an optical axis of a laser capture microdissection instrument; providing a transfer film carrier removably positioned in a transfer film carrier handling subsystem, the transfer film carrier having a substrate surface and a laser capture microdissection transfer film coupled to the substrate surface; and then placing the laser capture microdissection transfer film in juxtaposition with the sample by moving the transfer film carrier handling subsystem, the laser capture microdissection transfer film being placed in juxtaposition with a pressure sufficient to allow laser capture microdissection transfer of a portion of the sample to the laser capture microdissection transfer film, without forcing nonspecific transfer of a remainder of the sample to the laser capture microdisection film; and then transferring a portion of the sample to the laser capture microdissection transfer film, without forcing nonspecific transfer of a remainder of the sample to the laser capture microdissection transfer film. Transferring includes moving the laser capture microdissection transfer film and the portion of the sample away from the remainder of the sample with the transfer film carrier handling subsystem. The transfer film carrier handling subsystem can be mounted on an inverted microscope. The systems and methods provide the advantages of increased speed and much lower rates of contamination

5 Claims, 18 Drawing Sheets

U.S. PATENT DOCUMENTS

| | | | |
|---|---|---|---|
| 3,848,962 | 11/1974 | Nelson | 350/86 |
| 4,210,384 | 7/1980 | Meyer et al. | 350/19 |
| 4,303,866 | 12/1981 | Porro et al. | 250/442 |
| 4,436,385 | 3/1984 | Fischer et al. | 350/529 |
| 4,508,435 | 4/1985 | Graham et al. | 350/529 |
| 4,509,834 | 4/1985 | Hodgson | 350/521 |
| 4,538,885 | 9/1985 | Graham et al. | 350/529 |
| 4,552,033 | 11/1985 | Martzhauser | 74/479 |
| 4,600,282 | 7/1986 | Yamamura et al. | 353/122 |
| 4,614,431 | 9/1986 | Komeyama | 356/401 |
| 4,623,839 * | 11/1986 | Garretson et al. | |
| 4,627,009 | 12/1986 | Holmes et al. | 364/559 |
| 4,673,261 | 6/1987 | Hunt et al. | 350/331 |
| 4,702,565 | 10/1987 | Schilling et al. | 350/521 |
| 4,731,530 | 3/1988 | Mikan | 250/229 |
| 4,807,984 | 2/1989 | Kurimura et al. | 350/529 |
| 4,824,229 | 4/1989 | Narita et al. | 350/531 |
| 4,836,667 | 6/1989 | Ozeki | 350/531 |
| 4,852,985 | 8/1989 | Fujihara et al. | 350/523 |
| 4,856,873 | 8/1989 | Kleinberg | 350/502 |
| 4,871,245 | 10/1989 | Ishikawa et al. | 350/502 |
| 4,920,053 | 4/1990 | Inoue et al. | 435/240.1 |
| 4,923,294 | 5/1990 | Courtenay | 350/529 |
| 4,964,708 | 10/1990 | Mason | 350/519 |
| 4,992,660 | 2/1991 | Kobayashi | 250/306 |
| 5,029,791 | 7/1991 | Ceccon et al. | 248/287 |
| 5,057,689 | 10/1991 | Nomura et al. | 250/310 |
| 5,077,620 | 12/1991 | Mauro | 359/393 |
| 5,089,909 | 2/1992 | Kleinberg | 359/363 |
| 5,103,338 | 4/1992 | Crowley et al. | 359/394 |
| 5,126,877 | 6/1992 | Biber | 359/389 |
| 5,162,941 | 11/1992 | Favro et al. | 359/386 |
| 5,165,297 | 11/1992 | Krueger | 74/479 |
| 5,173,802 | 12/1992 | Heller | 359/384 |
| 5,173,803 | 12/1992 | Heller | 359/393 |
| 5,253,110 | 10/1993 | Ichihara et al. | 359/610 |
| 5,262,891 | 11/1993 | Nakasato | 359/385 |
| 5,263,384 | 11/1993 | Suzuki | 74/479 MF |
| 5,288,996 | 2/1994 | Betzig et al. | 250/227.26 |
| 5,296,963 | 3/1994 | Murakami et al. | 359/389 |
| 5,298,963 * | 3/1994 | Moriya et al. | |
| 5,312,393 | 5/1994 | Mastel | 606/4 |
| 5,323,009 | 6/1994 | Harris | 250/458.1 |
| 5,337,178 | 8/1994 | Kung et al. | 359/393 |
| 5,345,333 | 9/1994 | Greenberg | 359/389 |
| 5,357,366 | 10/1994 | Marchlenski | 359/393 |
| 5,359,417 | 10/1994 | Muller et al. | 356/375 |
| 5,367,401 | 11/1994 | Saulietis | 359/398 |
| 5,386,112 | 1/1995 | Dixon | 250/234 |
| 5,393,647 | 2/1995 | Neukermans et al. | 430/320 |
| 5,403,970 | 4/1995 | Aoki | 84/26 |
| 5,412,503 | 5/1995 | Nederlof | 359/393 |
| 5,420,716 | 5/1995 | Fukaya | 359/368 |
| 5,434,703 | 7/1995 | Morizumi | 359/385 |
| 5,450,233 | 9/1995 | Yamamoto et al. | 359/368 |
| 5,455,420 | 10/1995 | Ho et al. | 250/306 |
| 5,468,967 | 11/1995 | Chan et al. | 250/397 |
| 5,471,260 | 11/1995 | Luce et al. | 351/205 |
| 5,479,252 | 12/1995 | Worster et al. | 356/237 |
| 5,504,366 | 4/1996 | Weiss et al. | 73/863 |
| 5,506,725 | 4/1996 | Koike et al. | 359/388 |
| 5,510,615 | 4/1996 | Ho et al. | 250/306 |
| 5,517,353 | 5/1996 | Ikoh et al. | 359/388 |
| 5,532,476 | 7/1996 | Mikan | 250/221 |
| 5,532,873 | 7/1996 | Dixon | 359/388 |
| 5,535,052 | 7/1996 | Jorgens | 359/388 |
| 5,536,941 | 7/1996 | Swann | 250/311 |
| 5,537,863 | 7/1996 | Fujiu et al. | 73/105 |
| 5,552,928 | 9/1996 | Furuhashi et al. | 359/379 |
| 5,557,456 | 9/1996 | Garner et al. | 359/393 |
| 5,558,329 | 9/1996 | Liu | 273/148 B |
| 5,559,329 | 9/1996 | Joseph et al. | 250/300 |
| 5,587,748 | 12/1996 | Luce et al. | 351/208 |
| 5,587,833 | 12/1996 | Kamentsky | 359/300 |
| 5,598,888 | 2/1997 | Sullivan et al. | 165/263 |
| 5,602,674 | 2/1997 | Weissman et al. | 359/393 |
| 5,619,035 | 4/1997 | Weiss et al. | 250/306 |
| 5,621,207 | 4/1997 | O'Mara | 250/221 |
| 5,638,206 | 6/1997 | Sumiya et al. | 359/368 |
| 5,641,896 | 6/1997 | Karrai | 73/105 |
| 5,659,421 | 8/1997 | Rahmel et al. | 359/391 |

FOREIGN PATENT DOCUMENTS

| | | | |
|---|---|---|---|
| WO95/23960 | 9/1995 | (WO) | G01N/1/28 |
| WO97/13838 | 4/1997 | (WO) | C12M/1/26 |

OTHER PUBLICATIONS

Bielser, G. et al., "Cell surgery by laser micro–dissection: a preparative method", *Journal of Microscopy*, vol. 107, Pt. 1, May 1976, pp. 19–24.

Bonner, R. et al., "Laser Capture Microdissection: Molecular Anaylsis of Tissue", *Science*, vol. 278, Nov. 21, 1997, pp. 1481–1483.

Friend, T., "Getting up close to cancer genes", printed in *USA Today* newspaper, Science section, Aug. 5, 1997.

Schindler, M., "Select, microdissect, and eject", *Nature Biotechnology*, vol. 16, No. 8, Aug. 1998, pp. 719–720.

Schutze, K. et al., "Identification of expressed genes by laser–mediated manipulation of single cells", *Nature Biotechnology*, vol. 16, No. 8, Aug. 1998, pp. 737–742.

Meier–Ruge, W. et al., "The laser in the Lowry technique for microdissection of freeze–dried tissue slices", *Histochemical Journal*, vol. 8 (1976), pp. 387–401.

Kubo, Y. et al., "Early Detection of Knudson's Two–Hits in Preneoplastic Renal Cells of the Eker Rat Model by the Laser Microdissection Procedure", *Cancer Research*, vol. 55, No. 5, Mar. 1995, pp. 989–990.

Jimenez, C.R. et al., "Neuropeptide Expression and Processing as Revealed by Direct Matrix–Assisted Laser Desorption Ionization Mass Spectrometry of Single Neurons", *Journal of Neurochemistry*, vol. 62, No. 1, Jan. 1994, pp. 404–407.

Schindler, M. et al., Automated Analysis and Survival Selection of Anchorage–Dependent Cells Under Normal Growth Conditions, *Cytometry*, vol. 6, No. 4, Jul. 1985, pp. 368–374.

Fukui, K. et al., "Microdissection of plant chromosomes by argon–ion laser beam", *Theoretical and Applied Genetics*, vol. 84, No. 1–2, Jun. 1992, pp. 787–791.

Ashkin, A. et al., "Internal cell manipulation using infrared laser traps", *Proc. Natl. Acad. Sci. USA*, vol. 86, No. 20, Oct. 1989, pp. 7914–7918.

Veigel, C. et al., "New cell biological applications of the laser microbeam technique: the microdissection and skinning of muscle fibers and the perforation and fusion of sarcolemma vesicles", *European Journal of Cell Biology*, vol. 63, No. 1, Feb. 1994, pp. 140–148.

Geduspan, J. et al., "A Growth–Promoting Influence from the Mesonephros during Limb Outgrowth", *Developmental Biology*, vol. 151, No. 1, May 1992, pp. 242–250.

* cited by examiner

······ WHITE LIGHT ILLUMINATION PATH
—·—· LASER BEAM PATH

LASER CAPTURE MICRODISSECTION PRESSURE PLATE AND TRANSFER ARM

CROSS-REFERENCE TO RELATED APPLICATIONS

This application is, under 35 U.S.C. §120, a continuation of U.S. Ser. No. 09/018,452, filed Feb. 4, 1998, which is in-turn a continuation-in-part of both U.S. Ser. No. 60/060,731, filed Oct. 1, 1997, and U.S. Ser. No. 60/037,864, filed Feb. 7, 1997, now abandoned, the entire contents of all which are hereby incorporate herein by reference as if fully set forth herein.

BACKGROUND OF THE INVENTION

1. Field of the Invention

The invention relates generally to the field of laser capture microdisection (LCM). More particularly, the invention relates to inverted microscopes that include specialized apparatus for performing LCM. Specifically, a preferred implementation of the invention relates to an inverted microscope that includes a cap handling subsystem, an illumination/laser optical subsystem, a vacuum chuck subsystem, and a manual joystick subsystem. The invention thus relates to inverted microscopes of the type that can be termed laser capture microdisection inverted microscopes.

2. Discussion of the Related Art

Diseases such as cancer have long been identified by examining tissue biopsies to identify unusual cells. The problem has been that there has been no satisfactory prior-art method to extract the cells of interest from the surrounding tissue. Currently, investigators must attempt to manually extract, or microdissect, cells of interest either by attempting to mechanically isolate them with a manual tool or through a convoluted process of isolating and culturing the cells. Most investigators consider both approaches to be tedious, time-consuming, and inefficient.

A new technique has been developed which can extract a small cluster of cells from a tissue sample in a matter of seconds. The technique is called laser capture microdissection (LCM). Laser capture microdissection is a one-step technique which integrates a standard laboratory microscope with a low-energy laser and a transparent ethylene vinyl acetate polymer thermoplastic film such as is used for the plastic seal in food product packaging.

In laser capture microdissection, the operator looks through a microscope at a tissue biopsy section mounted on a standard glass histopathology slide, which typically contains groups of different types of cells. A thermoplastic film is placed over and in contact with the tissue biopsy section. Upon identifying a group of cells of interest within the tissue section, the operator centers them in a target area of the microscope field and then generates a pulse from a laser such as a carbon dioxide laser having an intensity of about 50 milliwatts (mW) and a pulse duration of between about 50 to about 500 milliseconds (mS). The laser pulse causes localized heating of the plastic film as it passes through it, imparting to it an adhesive property. The cells then stick to the localized adhesive area of the plastic tape directly above them, whereupon the cells are immediately extracted and ready for analysis. Because of the small diameter of the laser beam, extremely small cell clusters may be microdissected from a tissue section.

By taking only these target cells directly from the tissue sample, scientists can immediately analyze the gene and enzyme activity of the target cells using other research tools. Such procedures as polymerase chain reaction amplification of DNA and RNA, and enzyme recovery from the tissue sample have been demonstrated. No limitations have been reported in the ability to amplify DNA or RNA from tumor cells extracted with laser capture microdissection.

Laser capture microdissection has successfully extracted cells in all tissues in which it has been tested. These include kidney glomeruli, in situ breast carcinoma, atypical ductal hyperplasia of the breast, prostatic interepithielial neoplasia, and lymphoid follicles. The direct access to cells provided by laser capture microdissection will likely lead to a revolution in the understanding of the molecular basis of cancer and other diseases, helping to lay the groundwork for earlier and more precise disease detection.

Another likely role for the technique is in recording the patterns of gene expression in various cell types, an emerging issue in medical research. For instance, the National Cancer Institute's Cancer Genome Anatomy Project (CGAP) is attempting to define the patterns of gene expression in normal, precancerous, and malignant cells. In projects such as CGAP, laser capture microdissection is a valuable tool for procuring pure cell samples from tissue samples.

The LCM technique is generally described in the recently published article: Laser Capture Microdissection, *Science*, Volume 274, Number 5289, Issue 8, pp 998–1001, published in 1996, the entire contents of which are incorporated herein by reference. The purpose of the LCM technique is to provide a simple method for the procurement of selected human cells from a heterogeneous population contained on a typical histopathology biopsy slide.

A typical tissue biopsy sample consists of a 5 to 10 micron slice of tissue that is placed on a glass microscope slide using techniques well known in the field of pathology. This tissue slice is a cross section of the body organ that is being studied. The tissue consists of a variety of different types of cells. Often a pathologist desires to remove only a small portion of the tissue for further analysis.

LCM employs a thermoplastic transfer film that is placed on top of the tissue sample. This film is manufactured containing organic dyes that are chosen to selectively absorb in the near infrared region of the spectrum overlapping the emission region of common AlGaAs laser diodes. When the film is exposed to the focused laser beam the exposed region is heated by the laser and melts, adhering to the tissue in the region that was exposed. The film is then lifted from the tissue and the selected portion of the tissue is removed with the film.

Thermoplastic transfer films such as a 100 micron thick ethyl vinyl acetate (EVA) film available from Electroseal Corporation of Pompton Lakes, N.J. (type E540) have been used in LCM applications. The film is chosen to have a low melting point of about 90° C.

The thermoplastic EVA films used in LCM techniques have been doped with dyes, such as an infrared napthalocyanine dye, available from Aldrich Chemical Company (dye number 43296-2 or 39317-7). These dyes have a strong absorption in the 800 nm region, a wavelength region that overlaps with laser emitters used to selectively melt the film. The dye is mixed with the melted bulk plastic at an elevated temperature. The dyed plastic is then manufactured into a film using standard film manufacturing techniques. The dye concentration in the plastic is about 0.001M.

While the films employed in LCM applications have proved satisfactory for the task, they have several drawbacks. The optical absorption of a dye impregnated film is a function of its thickness. This property of the film may be in conflict with a desire to select film thickness for other reasons.

The organic dyes which are used to alter the absorption characteristics of the films may have detrimental photochemistry effects in some cases. This could result in contamination of LCM samples. In addition, the organic dyes employed to date are sensitive to the wavelength of the incident laser light and thus the film must be matched to the laser employed.

SUMMARY OF THE INVENTION

There is a particular need for an instrument that is well suited for laser capture microdissection. There is also a particular need for an improved method of laser capture microdissection.

A first aspect of the invention is implemented in an embodiment that is based on a laser capture microdissection method, comprising: providing a sample that is to undergo laser capture microdissection; positioning said sample within an optical axis of a laser capture microdissection instrument; providing a transfer film carrier having a substrate surface and a laser capture microdissection transfer film coupled to said substrate surface; placing said laser capture microdissection transfer film in juxtaposition with said sample with a pressure sufficient to allow laser capture microdissection transfer of a portion of said sample to said laser capture microdissection transfer film, without forcing nonspecific transfer of a remainder of said sample to said laser capture microdisection film; and then transferring a portion of said sample to said laser capture microdissection transfer film, without forcing nonspecific transfer of a remainder of said sample to said laser capture microdissection transfer film.

A second aspect of the invention is implemented in an embodiment that is based on a laser capture microdissection instrument, comprising: an inverted microscope including: an illumination/laser optical subsystem; a translation stage coupled to said illuminator/laser optical subsystem; a cap handling subsystem coupled to said translation stage; a vacuum chuck subsystem coupled to said translation stage; and a manual joystick subsystem coupled to said translation stage.

These, and other, aspects and objects of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

BRIEF DESCRIPTION OF THE DRAWINGS

A clear conception of the advantages and features constituting the invention, and of the components and operation of model systems provided with the invention, will become more readily apparent by referring to the exemplary, and therefore nonlimiting, embodiments illustrated in the drawings accompanying and forming a part of this specification, wherein like reference numerals (if they occur in more than one view) designate the same elements. Consequently, the claims are to be given the broadest interpretation that is consistent with the specification and the drawings. It should be noted that the features illustrated in the drawings are not necessarily drawn to scale.

DESCRIPTION OF PREFERRED EMBODIMENTS

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail.

The entire contents of U.S. Ser. No. 60/037,864, filed Feb. 7, 1997 entitled "Laser Capture Microdissection Device," (Docket No. ARCT-002); U.S. Ser. No. 08/797,026, filed Feb. 7, 1997; U.S. Ser. No. 08/800,882, filed Feb. 14, 1997; U.S. Ser. No. 60/060,731, filed Oct. 1, 1997; and U.S. Ser. No. 60/060,732, filed Oct. 1, 1997 are hereby expressly incorporated by reference into the present application as if fully set forth herein.

Figure 1:
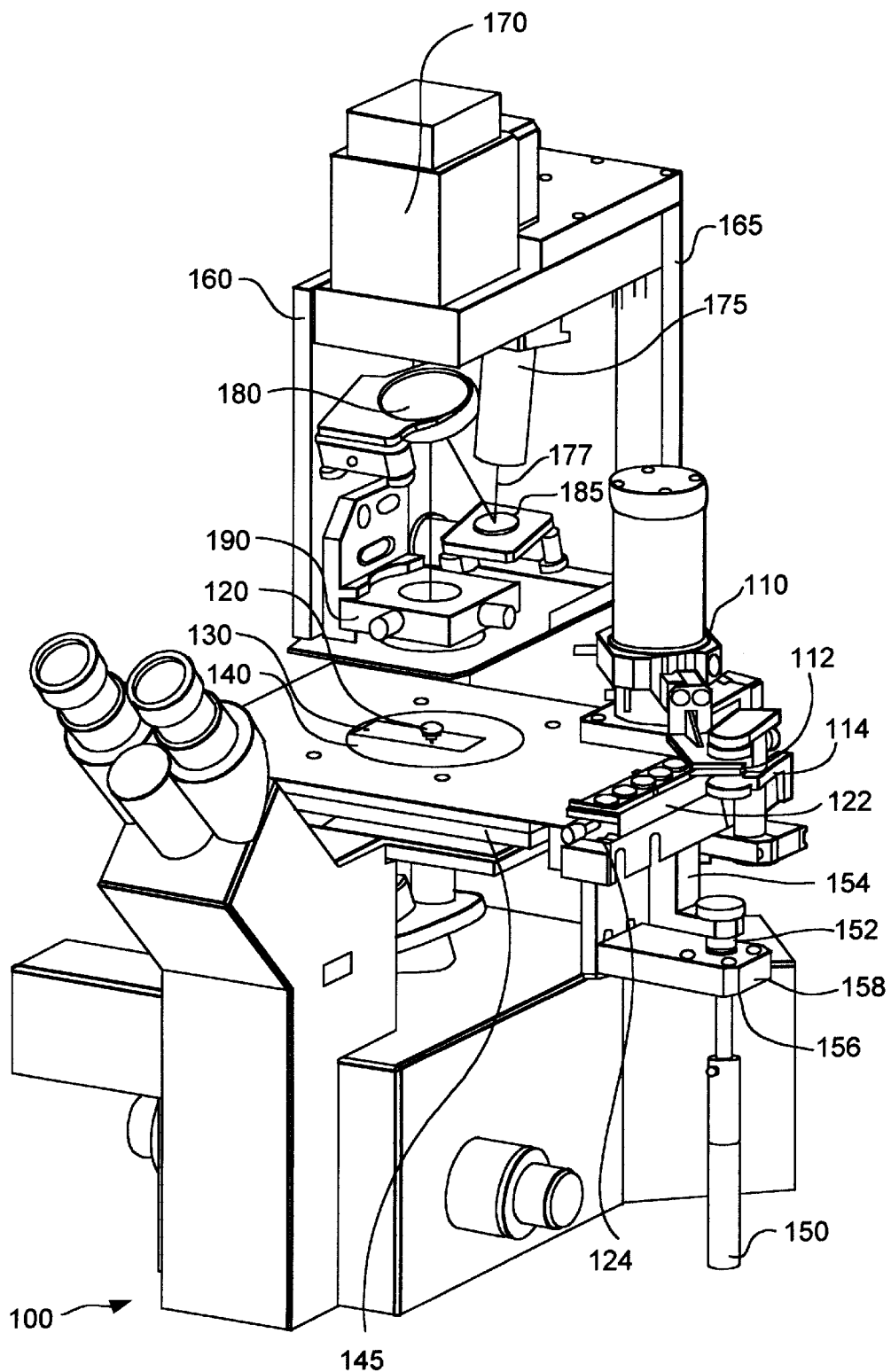
FIG. 1 illustrates a perspective view of a laser capture microdissection inverted microscope, representing an embodiment of the invention.

Turning to FIG. 1, a perspective view of an inverted microscope 100 for laser capture microdissection (LCM) is depicted. The inverted microscope 100 includes a variety of subsystems, particularly adapted for the LCM technique which combine to provide synergistic and unexpectedly good results. In alternative embodiments, the microscope does not need to be an inverted microscope.

A cap handling mechanic subassembly 110 provides structure for picking a microcentrifuge tube cap 120 from a supply 122 and placing the microcentrifuge tube cap 120 on top of a sample that is to undergo LCM. In the depicted embodiment, the microcentrifuge tube cap 120 is a cylindrical symmetric plastic cap and the supply 122 includes eight of the consumables on a dovetail slide 124. In the depicted embodiment, there is a laser capture microdissection transfer film coupled to the bottom of the microcentrifuge tube cap 120. The cap handling mechanic subassembly 110 is depicted in one of several possible positions wherein a working end 112 of the cap handling mechanic subassembly 110 is positioned in a vial capping station 114. The movement of the cap handling mechanic subassembly 110 will be described in more detail below.

A glass slide 130 upon which the sample to be microdissected is located and upon which the microcentrifuge tube cap 120 is placed, is located in the primary optical axis of the inverted microscope 100. In alternative embodiments, the slide that supports the sample can be made of other substantially transparent materials, for example, plastics such as polycarbonate. The glass slide 130 is supported and held in place by a vacuum chuck 140. The vacuum chuck 140 is a substantially flat surface that engages the glass slide 130 through a manifold (not shown) so as to hold the glass slide 130 in place while the microcentrifuge tube cap 120 is picked and placed and while a translation stage 145 is manipulated in an X-Y plane. In alternative embodiments, the translation stage can be configured so as to have the capability of being moved along a Z axis.

The translation stage 145 can be manipulated using a pair of rotary controls (not shown in FIG. 1). In addition, the translation stage 145 can be manipulated using a joystick 150. The joystick 150 is connected to the translation stage 145 through a spherical mounting 152 and a bracket 154. The joystick 150 includes a second spherical mounting 156 within a static bracket 158. The joystick provides simultaneous X and Y movement. Further, this simultaneous movement can be effected with in a single handed manner. The acquisition of samples is thus made quicker.

Mechanical leverage is provided by the fact that the length between the spherical mounting 152 and the second spherical mounting 156 is less than the length between the second spherical mounting 156 and the bottom end of the joystick 150. This leverage ratio is not needed for multiplication of force, but for the reduction in scalar movement. This ratio should be less than 1/5, preferably approximately 1/7. This ratio can be adjusted to provide the optimal resolution needed in terms of sample movement as a function of operator hand movement.

In addition, the joystick provides tactile feedback not available with electronic controls or geared linkages. The joystick 150 permits simultaneous movement of the translation stage 145 in two directions (X and Y) as a function of a single vector movement of an operator's hand. This important feature provides an unexpected result in that the speed with which features to be microdissected can be positioned in the principal optical axis of the inverted microscope 100 is significantly increased.

Still referring to FIG. 1, the inverted microscope 100 includes an LCM optical train 160. The LCM optical train 160 is mounted on an illumination arm 165. A white light illuminator 170 is also mounted on the illumination arm 165. White light from the illuminator 170 passes downward toward the microcentrifuge tube cap 120 through a dichroic mirror 180 and a focusing lens 190. A laser diode 175 with collimating optics emits a beam 177 that is reflected by a beam steering mirror 185. After the beam 177 is reflected by the beam steering mirror 185 it is incident upon the dichroic mirror 180. The dichroic mirror 180 is a dichroic that reflects the beam 170 downward through the focusing lens 190 toward the microcentrifuge tube cap 120. Simultaneously, the dichroic mirror 180 allows white light from the illuminator 170 to pass directly down through the focusing lens 190 toward the microcentrifuge tube cap 120. Thus, the beam 177 and the white light illumination are superimposed. The focusing lens 190 also adjusts the beam spot size.

Figure 2B:
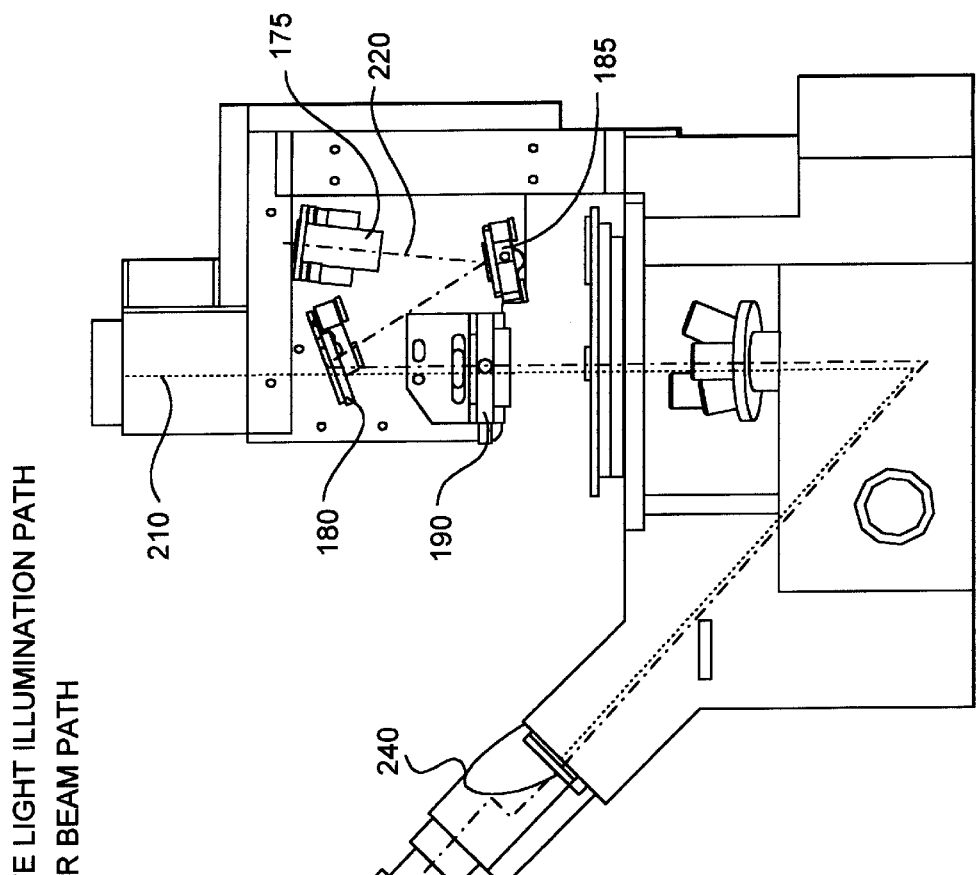
FIGS. 2A–2B illustrate orthographic views of the laser capture microdissection (LCM) inverted microscope shown in FIG. 1.
Figure 2A:
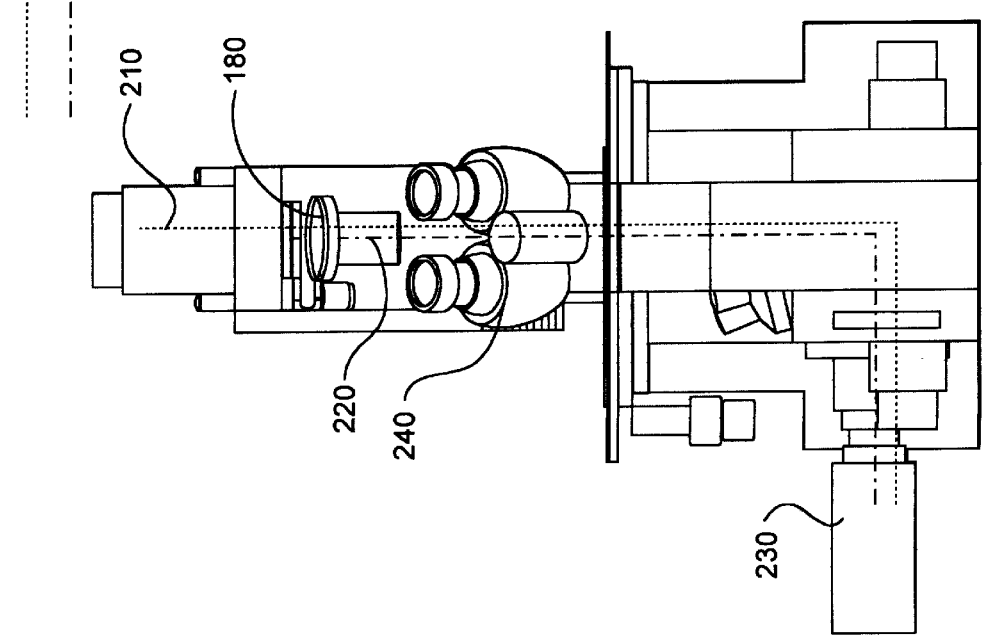

Turning now to FIGS. 2A–2B, two orthographic views of the apparatus depicted in FIG. 1 are illustrated. A white light illumination path 210 and a laser beam path 220 can be seen in both FIGS. 2A and 2B. It can be appreciated from FIG. 2A that both of the paths include delivery of optical information to an image acquisition system 230. Similarly, it can be appreciated from FIG. 2B that the illumination beam path includes delivery of optical information to a binocular set 240. In alternative embodiments, the eyepiece assembly (i.e., ocular) can include a monocular.

Figure 3:
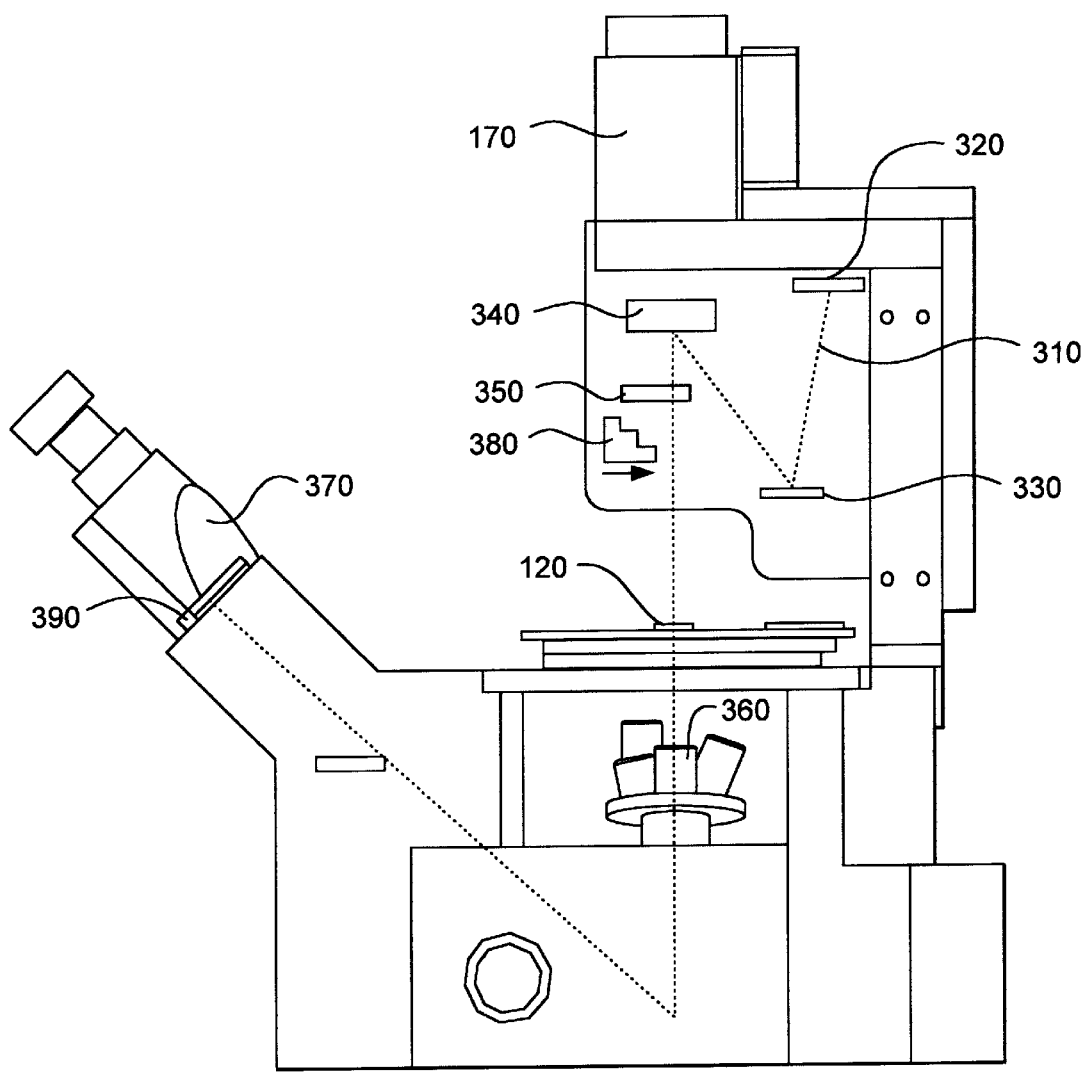
FIG. 3 illustrates a partial cross-sectional view of an LCM inverted microscope, representing an embodiment of the invention.

Turning to FIG. 3, a block schematic diagram of an optical train according to the invention is depicted. A laser beam path 310 begins at a film activation laser 320. The laser beam path 310 is then reflected by a mirror 330. The laser beam path 310 is then reflected by a dichroic mirror 340. The laser beam path 310 is then focused by a lens 350. The lens 350 can optionally be associated with structure for changing the beam diameter such as, for example, a variable aperture. The laser beam path 310 then passes downward toward the microcentrifuge tube cap 120. The laser beam path 310 then passes through an objective lens 360 and is then reflected. A cut-off filter 390 is installed in the ocular 370. The cut-off filter 390 can reflect and/or absorb the energy from the laser beam.

The position of the laser beam path 310 with respect to the portion of the sample that is to be acquired by the microcentrifuge tube cap 120 can be seen by an operator via the image acquisition system 230 (not shown in FIG. 3), which can include a camera. In idle mode, the laser beam path 310 provides a visible low amplitude signal that can be detected via the acquisition system 230. In pulse mode, the laser beam path 310 delivers energy to the microcentrifuge tube cap 120 and the optical characteristics of the cut-off filter 390 attenuate the laser beam path 310 sufficiently so that substantially none of the energy from the laser beam exits through ocular 370.

Suitable laser pulse widths are from 0 to approximately 1 second, preferably from 0 to approximately 100 milliseconds, more preferably approximately 50 milliseconds. In a preferred embodiment the wavelength of the laser is 810 nannometers. In a preferred embodiment the spot size of the laser at the EVA material located on microcentrifuge tube cap 120 is variable from 0.1 to 100 microns, preferably from 1 to 60 microns, more preferably from 5 to 30 microns. These ranges are relatively preferred when designing the optical subsystem. From the standpoint of the clinical operator, the widest spot size range is the most versatile. A lower end point in the spot size range on the order of 5 microns is useful for transferring single cells.

Suitable lasers can be selected from a wide power range. For example, a 100 watt laser can be used. On the other hand, a 50 mW laser can be used. The laser can be connected to the rest of the optical subsystem with a fiber optical coupling. Smaller spot sizes are obtainable using diffraction limited laser diodes and/or single mode fiber optics. Single mode fiber allows a diffraction limited beam.

While the laser diode can be run in a standard mode such as $TEM_{00}$, other intensity profiles can be used for different types of applications. Further, the beam diameter could be changed with a stepped lens instead of lens 350.

Changing the beam diameter permits the size of the portion of the sample that is acquired to be adjusted. Given a tightly focused initial condition, the beam size can be increased by defocusing. Given a defocused initial condition, the beam size can be decreased by focusing. The change in focus can be in fixed amounts. The change in focus can be obtained by means of indents on a movable lens mounting and/or by means of optical glass steps. In any event, increasing/decreasing the optical path length is the effect that is needed to alter the focus of the beam, thereby altering the spot size. For example, inserting a stepped glass prism 380 into the beam so the beam strikes one step tread will change the optical path length and alter the spot size.

Figure 4:
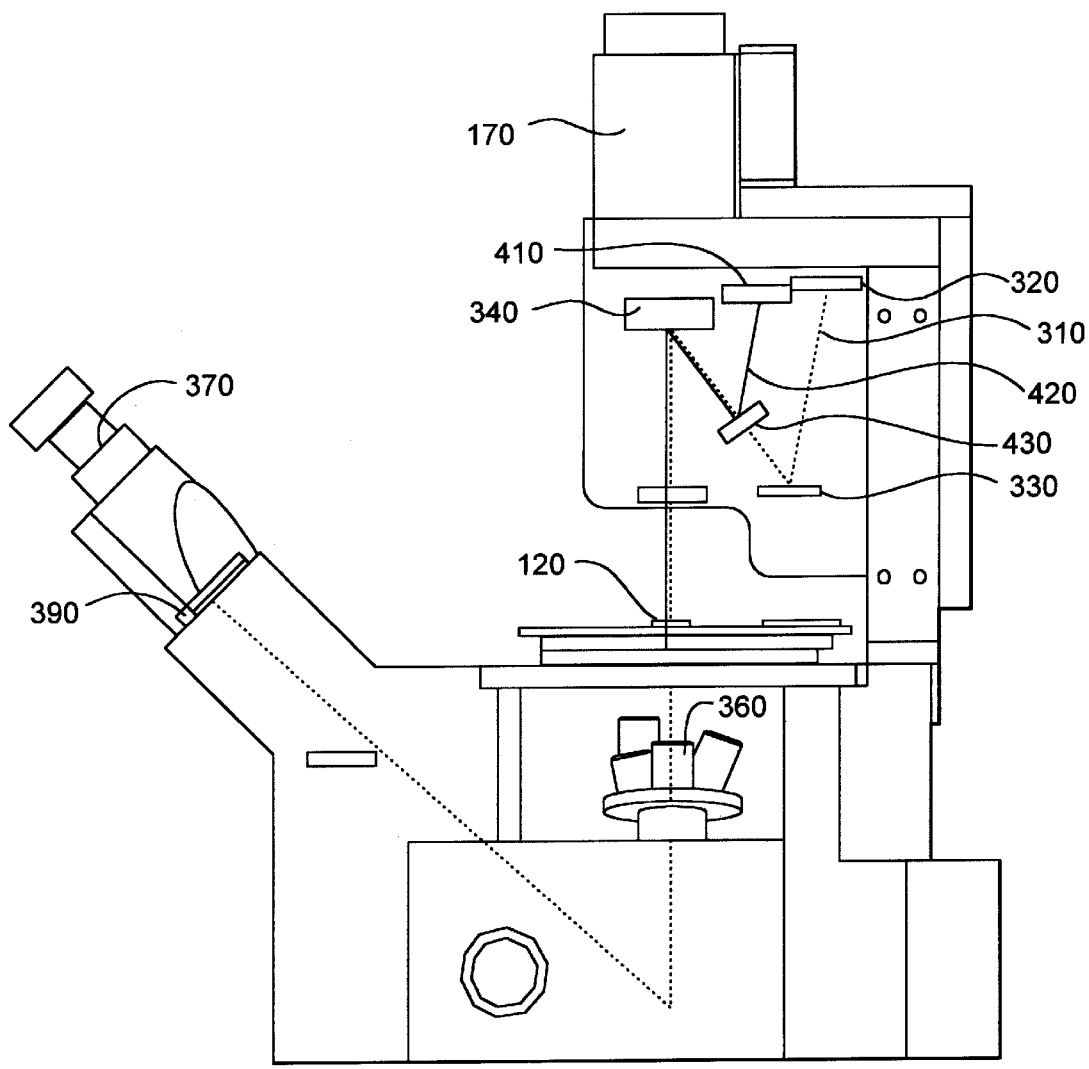
FIG. 4 illustrates a partial cross-sectional view of an LCM inverted microscope, representing an embodiment of the invention.

Turning now to FIG. 4, a schematic block diagram of another embodiment of an instrument according to the invention is depicted. In this embodiment, a light source 410 (e.g., fluorescence laser), emits a specific wavelength or wavelength range. The specific wavelength or wavelength range of a beam 420 emitted by the light source 410 is chosen, or filtered, to excite a fluorescent system (e.g., chemical markers and optical filtering techniques that are known in the industry) that is incorporated in or applied to the sample to be microdissected. The frequency of a beam 420 emitted by the fluorescence laser 410 can be tuned. The sample includes at least one member selected from the group consisting of chromophores and fluorescent dyes (synthetic or organic), and, the process of operating the instrument includes identifying at least a portion of said sample with light that excites the at least one member, before the step of transferring said portion of said sample to said laser capture microdissection transfer film.

Still referring to FIG. 4, the beam 420 is reflected by a mirror 430. The beam 420 is then reflected by the dichroic mirror 340. In this way the beam 420 can be made coincident with both the laser beam path 310 and the white light from illuminator 170. It should be noted that the beam 420 and the laser beam path 310 are shown in a spaced-apart configuration for clarity only. The beam 420 and the laser beam path 310 can be coaxial. Fluorescence emitted by the sample beneath the microcentrifuge tube cap 120 then travels through the objective lens 360 to be viewed by the operator through ocular 370.

Figure 5:
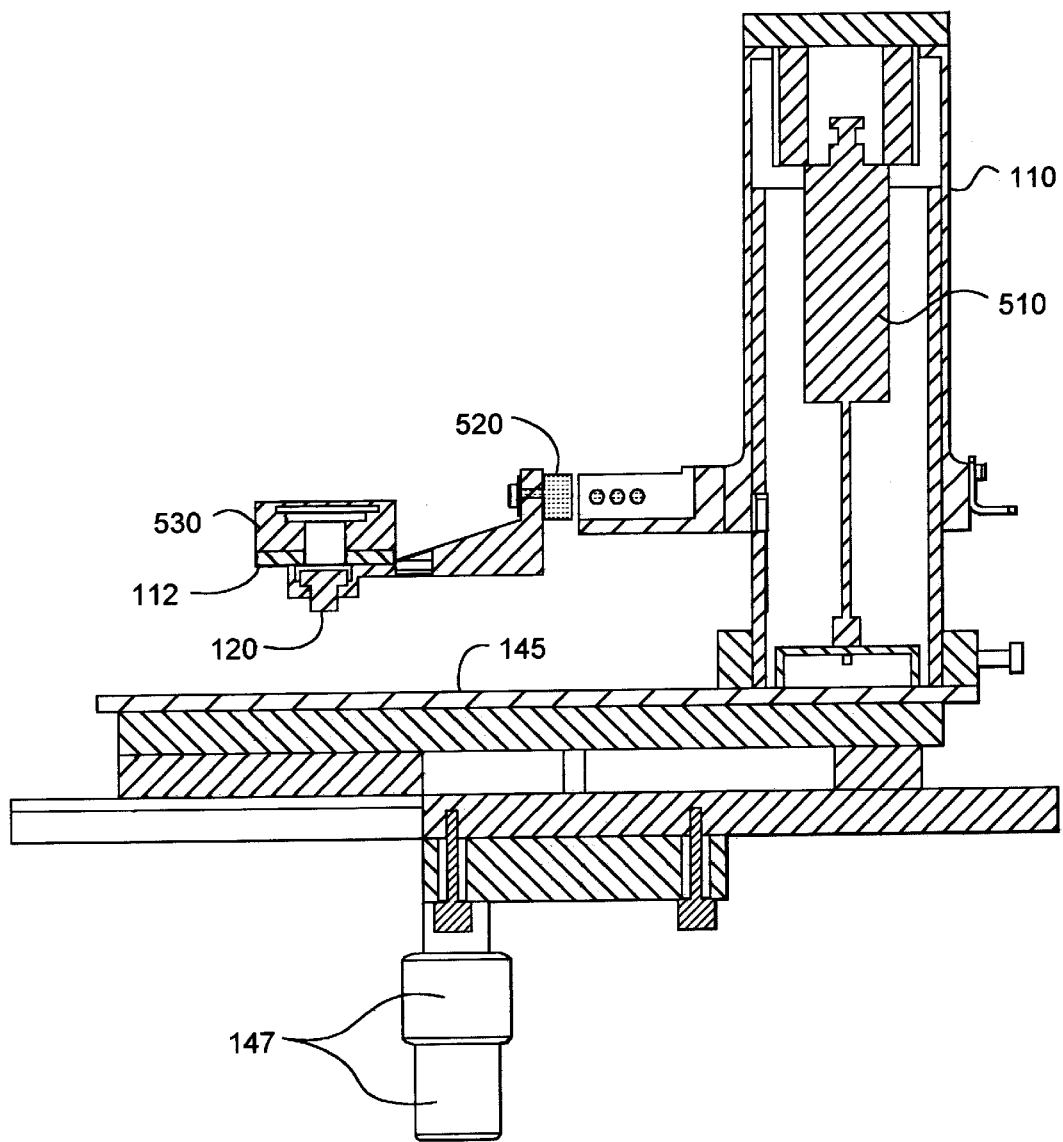
FIG. 5 illustrates a cross-sectional view of a cap handling subassembly, representing an embodiment of the invention.

Turning now to FIG. 5, a cross-sectional view of the cap handling mechanic subassembly 110 is depicted. The cap handling mechanic subassembly 110 includes a dampener 510. The dampener 510 is a structure for damping vertical motion of the cap handling mechanic subassembly 110. The dampener 510 is adapted to lower the microcentrifuge tube cap 120 down towards the translation stage in a reproducible manner. The dampener 510 can be an air dampener (e.g., pneumatic tube) or liquid dampener (e.g., hydraulic tube) or any other dynamic structure capable or retarding the vertical motion of the subassembly 110 so as not to generate an impulse. As the microcentrifuge tube cap 120 contacts the slide on which the sample rests (not shown), the working end 112 of an arm 520 that is coupled to the dampener 510 continues downward at a reproducible rate. Therefore, the top of the microcentrifuge tube cap 120 rises relative to the bottom of a weight 530. It can be appreciated that the cap 120 contacts the slide, before the weight 530 contacts the cap 120. In this way, the microcentrifuge tube cap 120 undergoes a self-leveling step before it is contacted and pressed against the slide by weight 530. As the weight 530 contacts the microcentrifuge tube cap 120 the working end 112 of arm 520 continues along its downward path. Therefore, the application of the weight 530 to microcentrifuge tube cap 120 is also a self-leveling step. By controlling the mass of weight 530, the force per unit area between the bottom of the microcentrifuge tube cap 120 and the slide can be controlled. After the sample on the slide has undergone LCM, the arm 520 can be raised. By raising the arm, the weight 530 is first picked off the microcentrifuge tube cap 120 and then the microcentrifuge tube cap 120 is picked up off of the slide. The dampener within the mechanism acts as a dash pot to control the velocity of the pickup arm.

The position of the translation stage is independent relative to the position of the cap handling mechanic subassembly 110. These relative positions can be controlled by the pair of rotary controls 147. It is to be noted that the pair of rotary controls 147 are depicted with their axes parallel to the axis of the microcentrifuge tube cap 120 in FIG. 5. However, the pair of rotary controls 147 can be configured in any orientation through the use of mechanical linkages such as gears.

Figure 6:
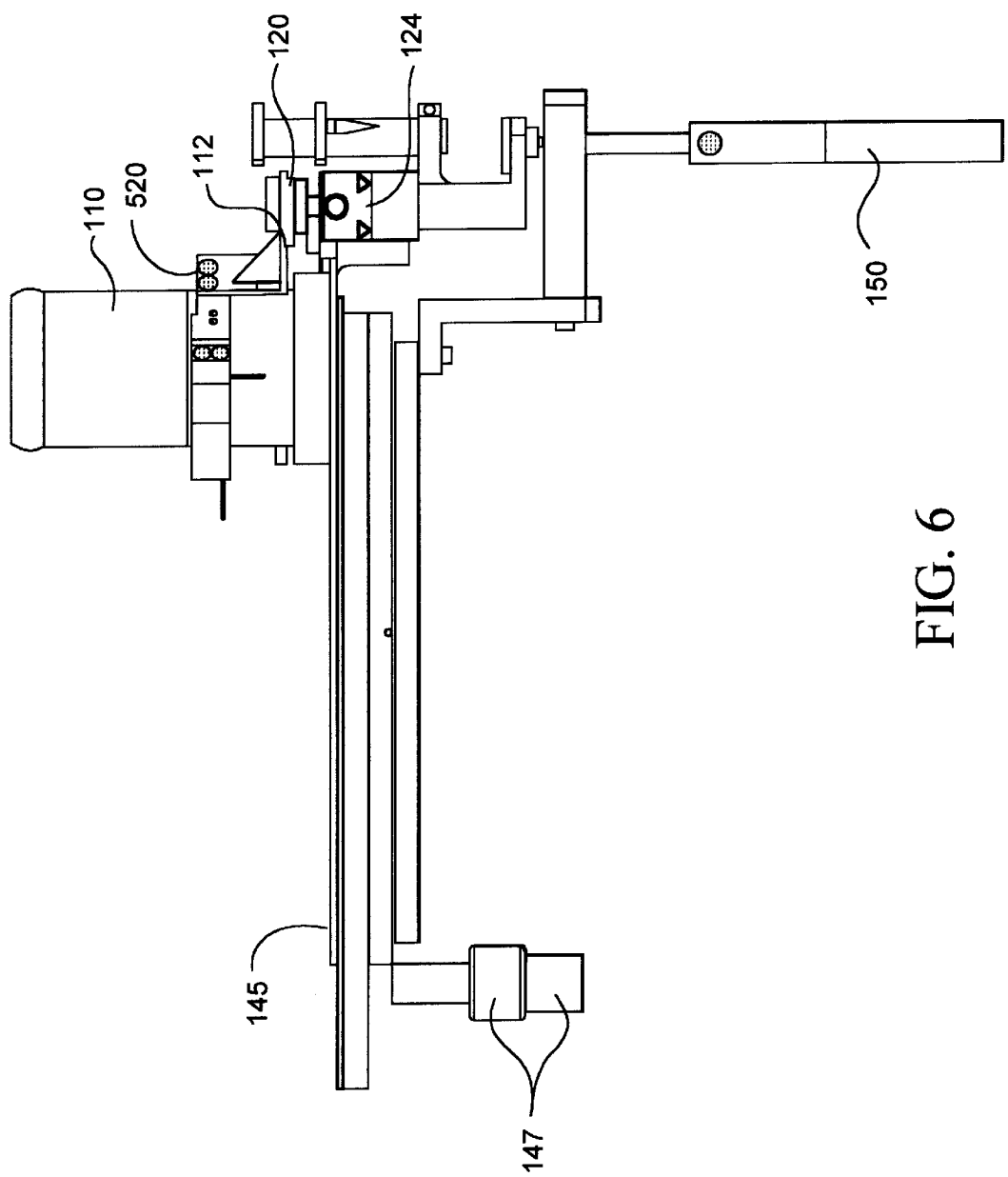
FIG. 6 illustrates an elevational view of a cap handling subassembly in a load position, representing an embodiment of the invention.

Turning now to FIG. 6, the cap handling mechanic subassembly 110 is depicted in a load position. In the load position, the working end 112 of the arm 520 is located directly over the dovetail slide 124. In this position, the working end 112 grasps a microcentrifuge tube cap 120. After grasping the microcentrifuge tube cap 120, the arm 520 is raised, thereby picking the microcentrifuge tube cap 120 up.

Figure 7:
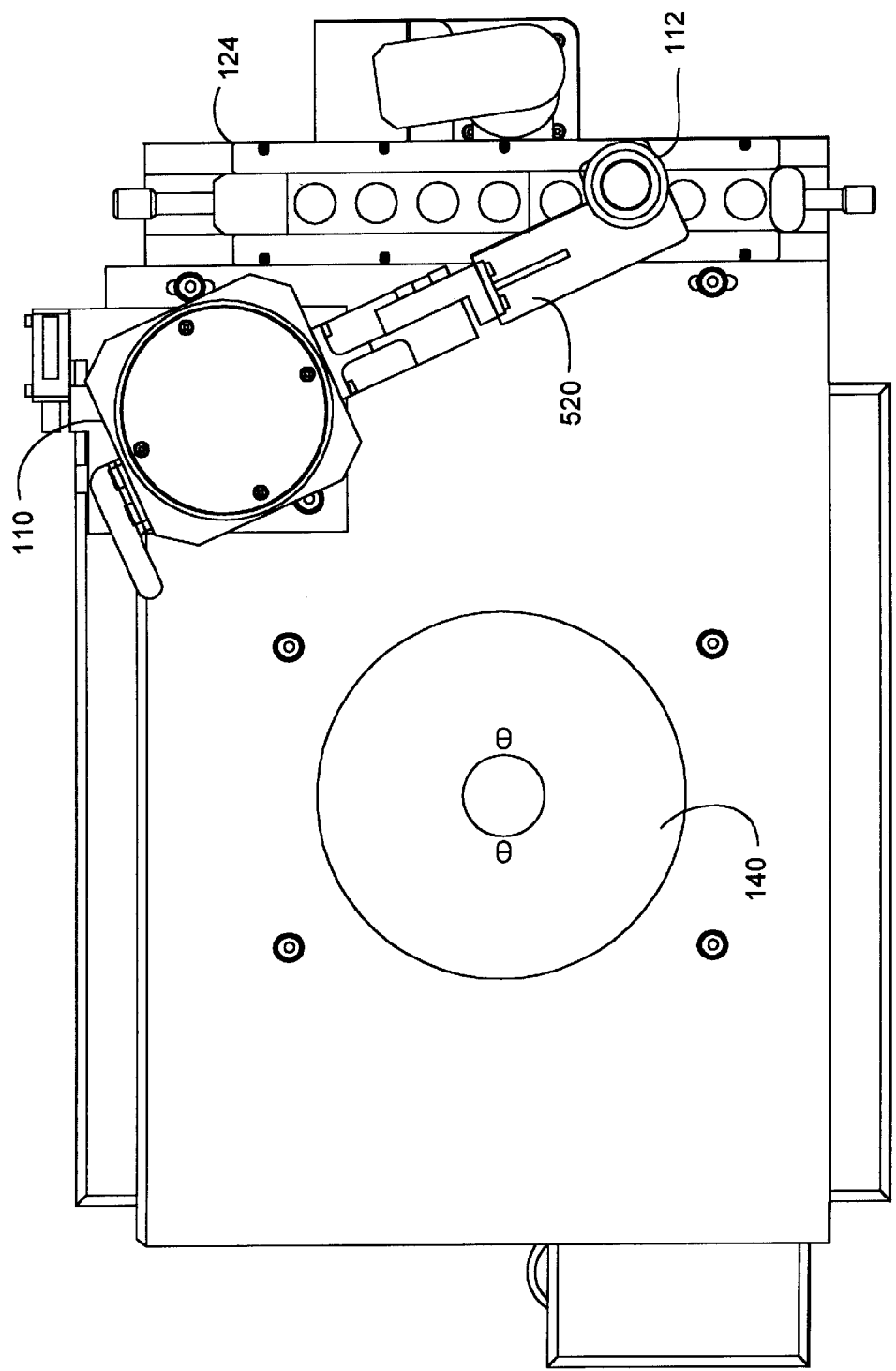
FIG. 7 illustrates a top plan view of the apparatus in the position depicted in FIG. 6.

Turning now to FIG. 7, a top plan view of the cap handling mechanic subassembly 110 in the load position can be seen. Before the arm 520 is swung into the load position, a fresh microcentrifuge tube cap is located beneath the axis of the working end 112. After the arm 520 is swung clockwise toward the vacuum chuck 140, the caps on dovetail slide 124 will be advanced so as to position a fresh microcentrifuge tube cap in place for the next cycle.

Figure 8:
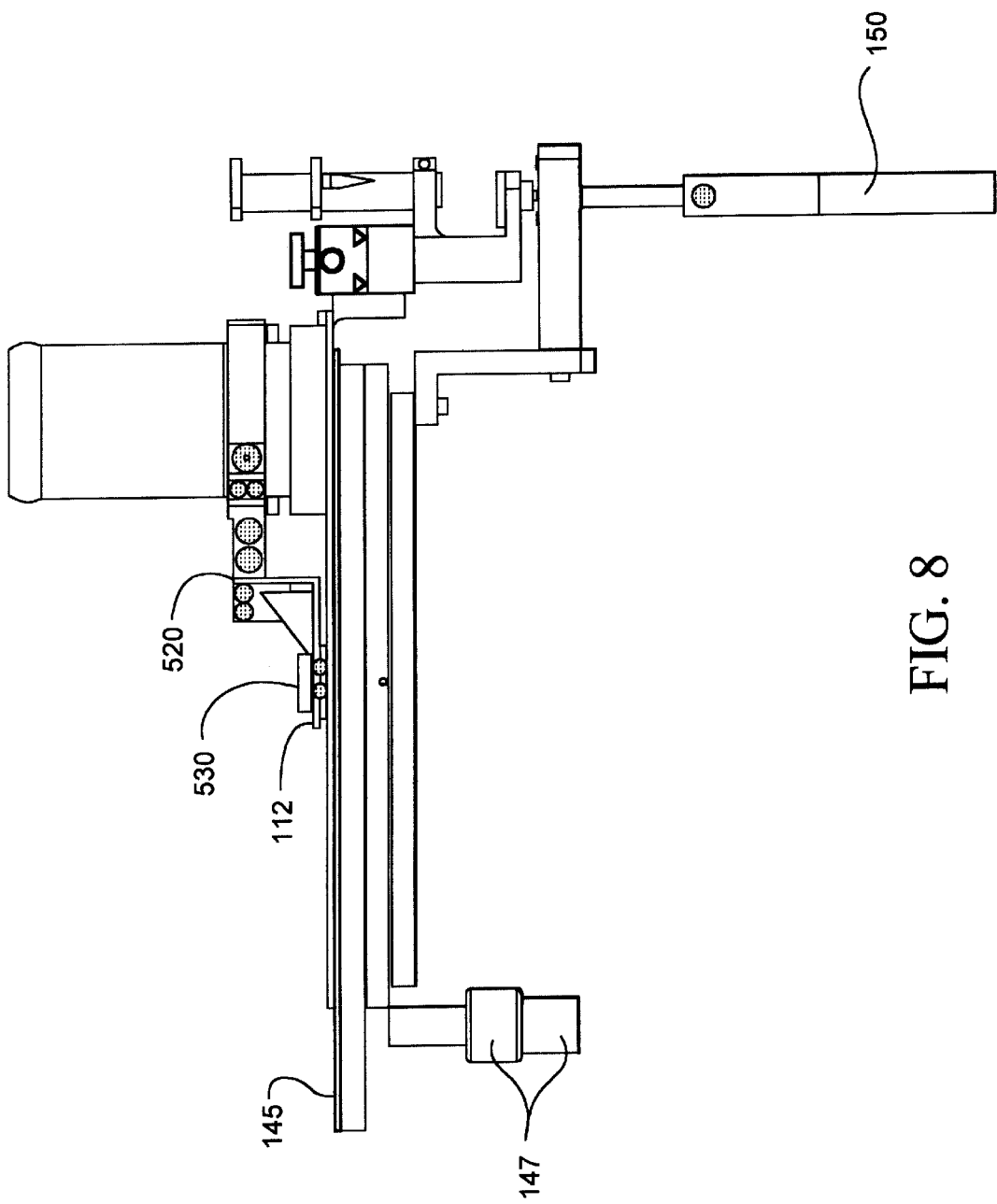
FIG. 8 illustrates an elevational view of a cap handling subassembly in an inspect position, representing an embodiment of the invention.

Turning now to FIG. 8, the cap handling mechanic subassembly 110 is depicted in an inspect position. When positioned in the inspect position, the working end 112 of the arm 520 is located coincident with the principal optical axis of the instrument. This is the position in which the arm 520 is lowered to permit first the self-leveling of the microcentrifuge tube cap 120 and then the self-leveling of the weight 530 on top of the microcentrifuge tube cap 120. After LCM, the arm 520 is raised in this position to put the weight 530 off the microcentrifuge tube cap 120 and then the microcentrifuge tube cap 120 off the slide (not shown).

The weight 530 is a free floating weight so that when it is set on top of the cap, the cap and weight are free to settle. The free floating weight permits the even application of pressure. For example, a weight of 30 grams can be used in the case where the total surface area of the laser capture microdissection transfer film is approximately 0.26 square inches.

Figure 9:
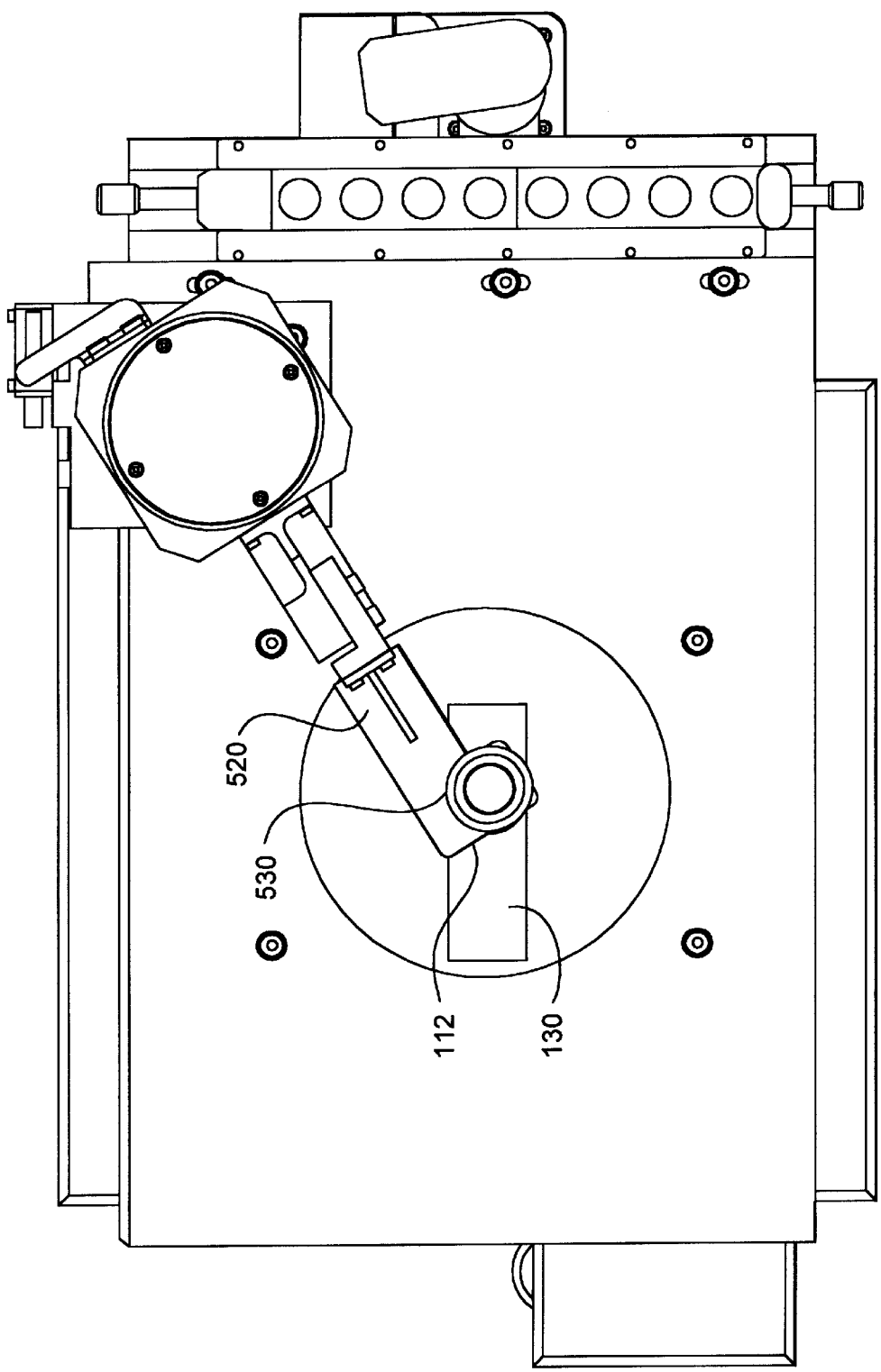
FIG. 9 illustrates a top plan view of the apparatus in the position depicted in FIG. 8.

Referring now to FIG. 9, a top plan view of the cap handling mechanic subassembly 110 in the inspect position is depicted. It can be appreciated from this view that the working end 112 of the arm 520 is located above the glass slide 130.

Figure 10:
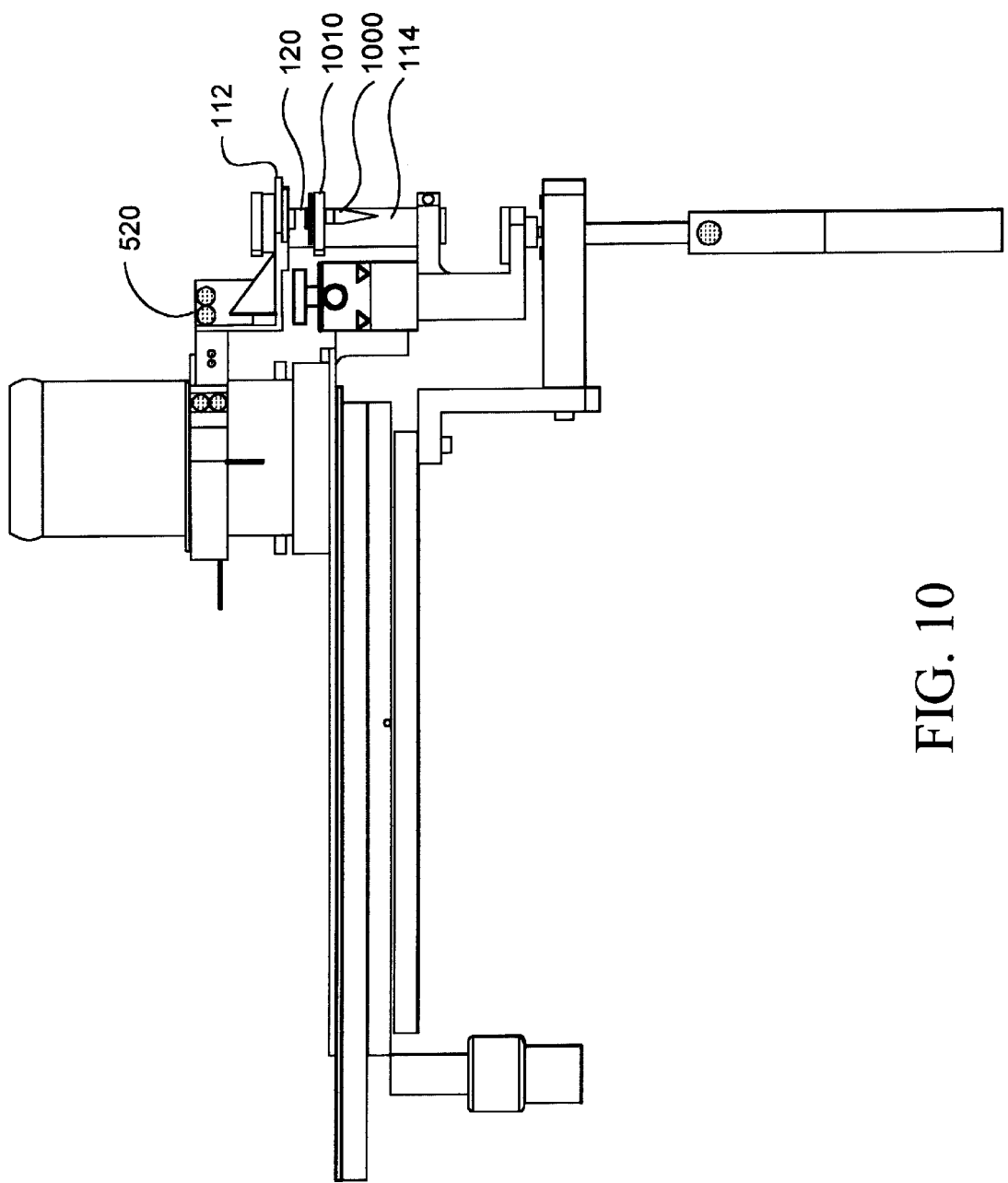
FIG. 10 illustrates an elevational view of a cap handling subassembly in an unload position, representing an embodiment of the invention.

Turning now to FIG. 10, the cap handling mechanic subassembly 110 is depicted in an unload position. In the unload position, the working end 112 of the arm 520 and the cap 120 (aka consumable) with the LCM attached tissue are all located above the vial capping station 114. After being positioned on axis with the vial capping station 114, the microcentrifuge tube cap 120 is lowered directly down onto, and into, an analysis container 1000. After the microcentrifuge tube cap 120 is inserted into the analysis container 1000, the working end 112 of the arm 520 is raised up. The working end 112 of the arm 520 is then rotated in a clockwise direction until it is above a fresh consumable (corresponding to the position depicted in FIGS. 6–7).

Figure 11:
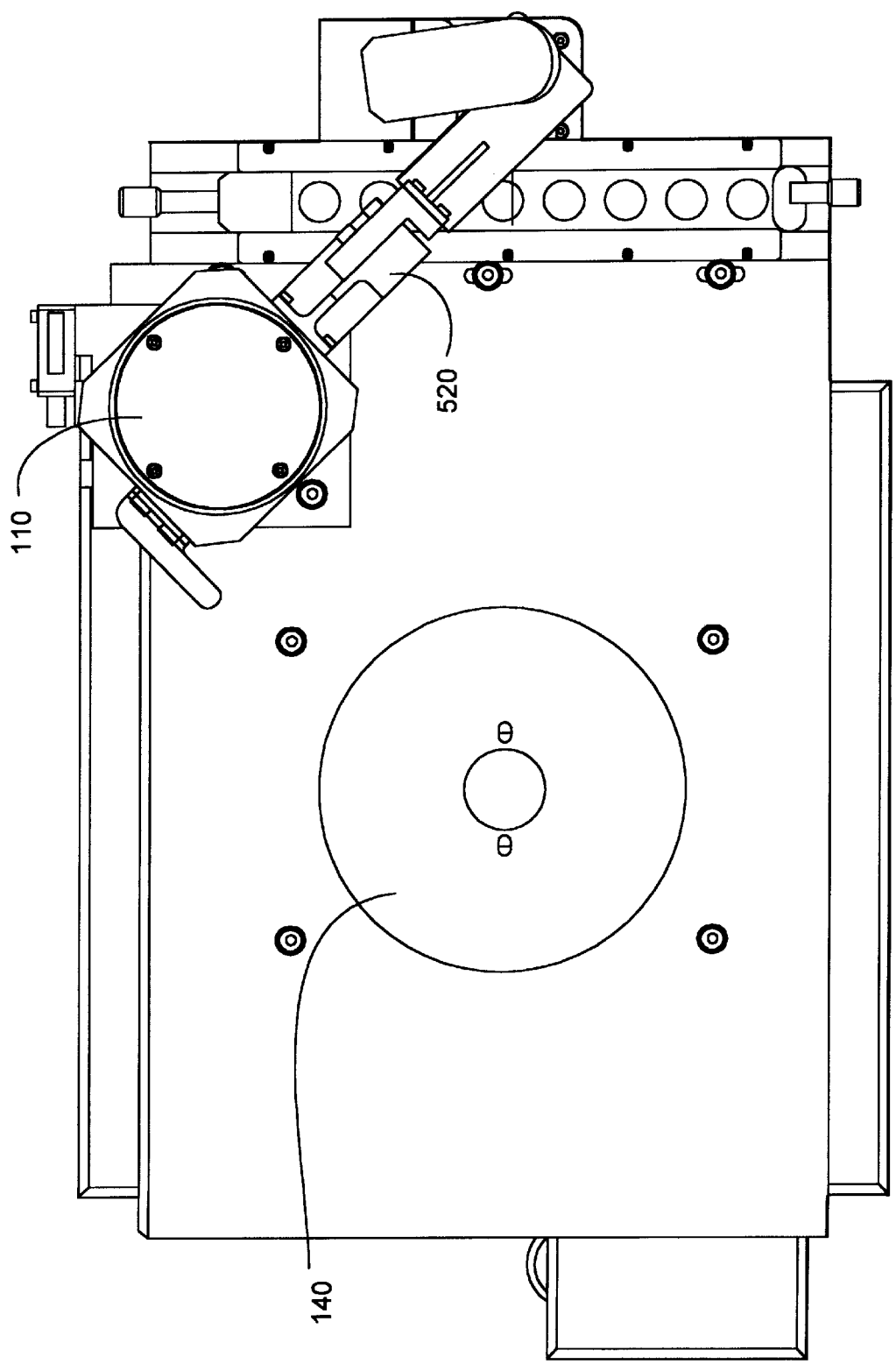
FIG. 11 illustrates a top plan view of the apparatus in the position depicted in FIG. 10.

Turning now to FIG. 11, a top plan view of the cap handling mechanic subassembly 110 in the unload position is depicted. In this position, the arm 520 is positioned away from the vacuum chuck 140. The analysis container 1000 (not visible in FIG. 11) is pushed upward so as to engage the microcentrifuge tube cap 120 (not visible in FIG. 11). The resultant sealed analysis container 1000 is then allowed to free fall back into a supporting bracket 1010 (see FIG. 10). The sealed analysis container 1000 together with the microcentrifuge tube cap 120 can then be taken from the bracket 1010 either manually or automatically.

Figure 12:
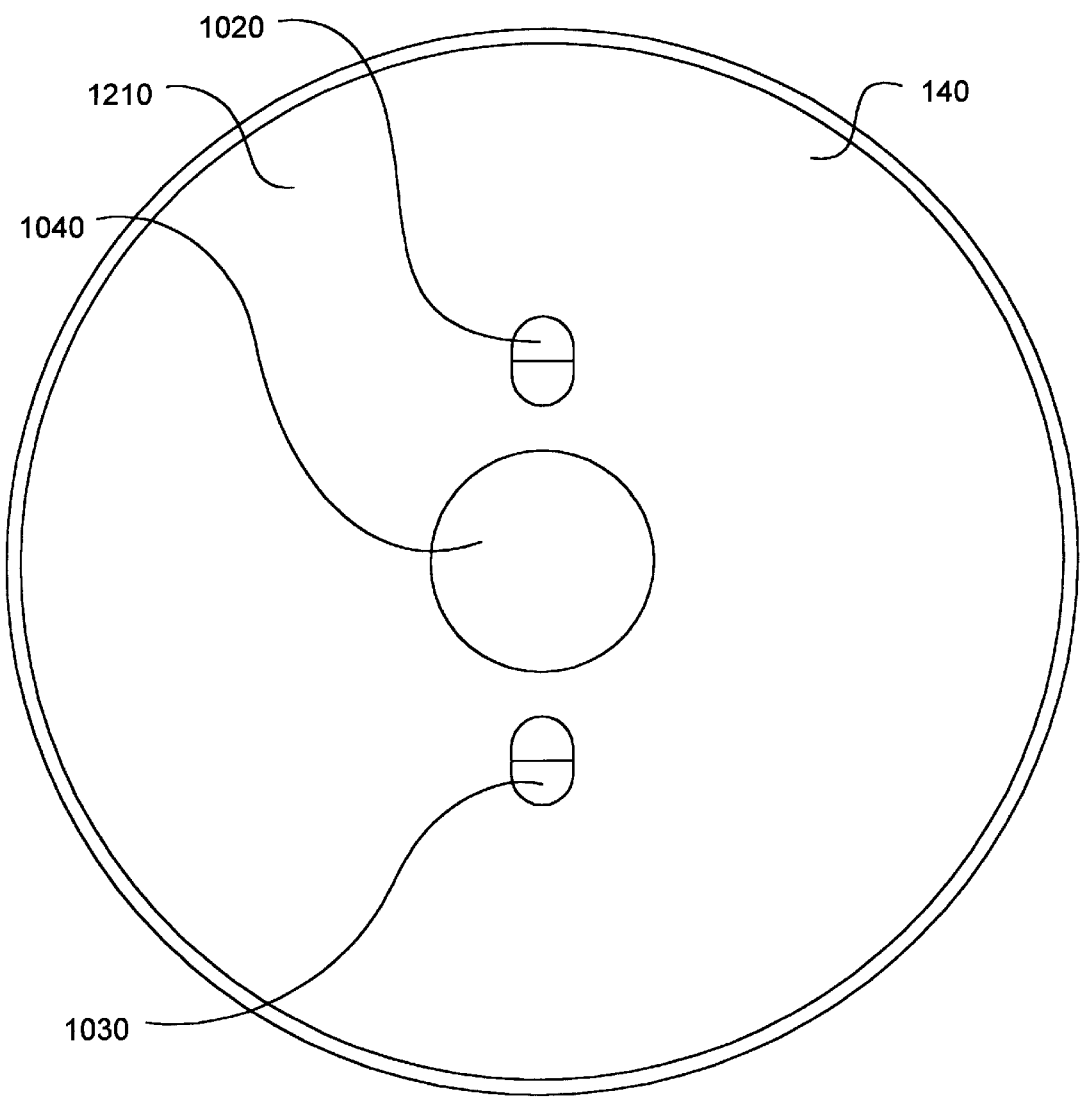
FIG. 12 illustrates a top plan view of a vacuum chuck, representing an embodiment of the invention.

Turning now to FIG. 12, a top plan view of the vacuum chuck 140 is depicted. A top surface 1210 of the vacuum chuck 140 includes a first manifold hole 1020 and a second manifold hole 1030. In alternative embodiments, there can be any number of manifold holes. The vacuum chuck 140 includes a beam path hole 1040. When the instrument is in operation, the glass slide (not shown), or other sample holder, is placed over the beam path hole 1040 and the manifold holes 1020–1030. After the glass slide is placed in position, a vacuum is pulled through a manifold connected to the holes 1020–1030, thereby holding the glass slide in position over the beam path hole 1040. Although a medium or even a high vacuum can be applied, a low vacuum is sufficient to hold the glass slide in place during the LCM process. A sufficient vacuum can even be generated with an inexpensive aquarium pump run in reverse.

The holding force exerted on the glass slide 130 is a function of the applied vacuum, the size and shape of the manifold holes 1020–1030 and the spacing between the top surface of the translation stage and the bottom surface of the glass slide 130. The spacing between the translation stage and the glass slide 130 is a function of the flatness of the surfaces and the elasticity of the corresponding structures.

The level of vacuum is adjusted so that the glass slide 130, or other sample carrier, can be translated with regard to the translation stage. This translation capability is present when the vacuum is off and when the vacuum is on.

There is some leakage around the perimeter of the glass slide 130 which modulates the force holding the glass slide 130 in place. Accordingly, a moderate force (e.g., 5 pounds) applied to the edge of the glass slide is sufficient to cause movement of the glass slide 130 with regard to the translation stage when the vacuum is engaged.

Figure 13:
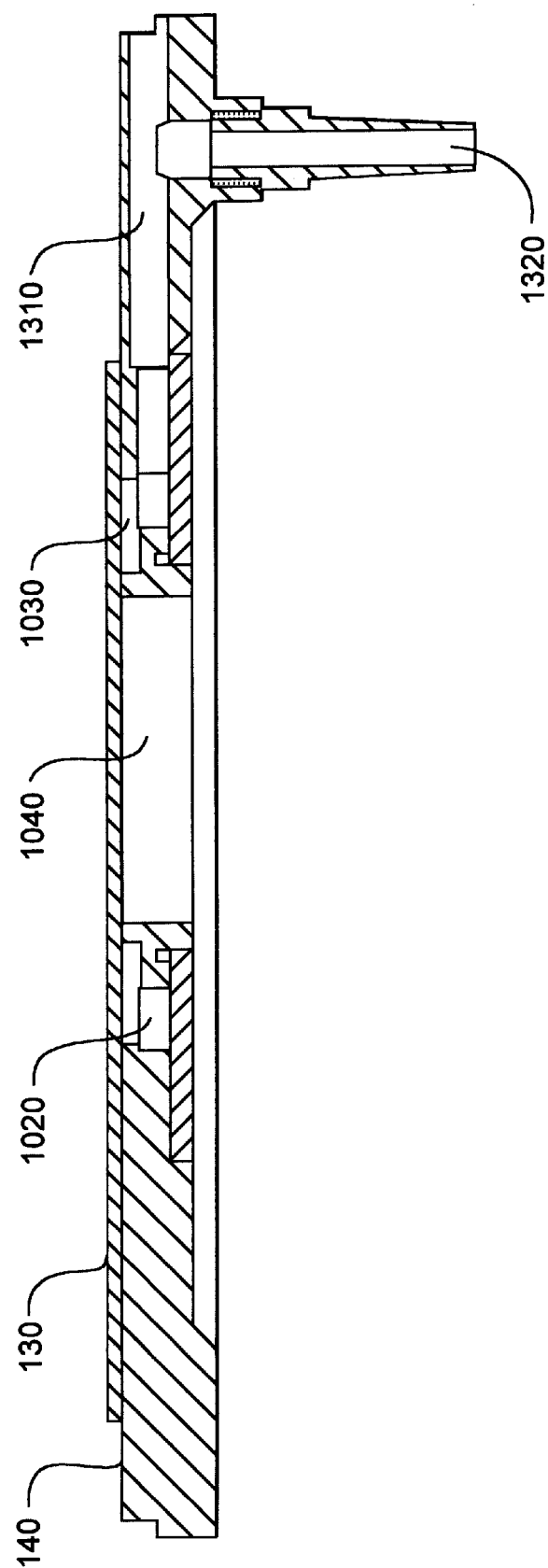
FIG. 13 illustrates a cross-sectional view of a vacuum chuck, representing an embodiment of the invention.

Turning now to FIG. 13, a cross section of the vacuum chuck is depicted with a glass slide 130 in place. The vacuum that holds the glass slide 130 in place is pulled through conduit 1320. The conduit 1320 is connected to a circular manifold 1310. The circular manifold 1310 is coupled with the manifold holes 1020–1030.

Figure 14:
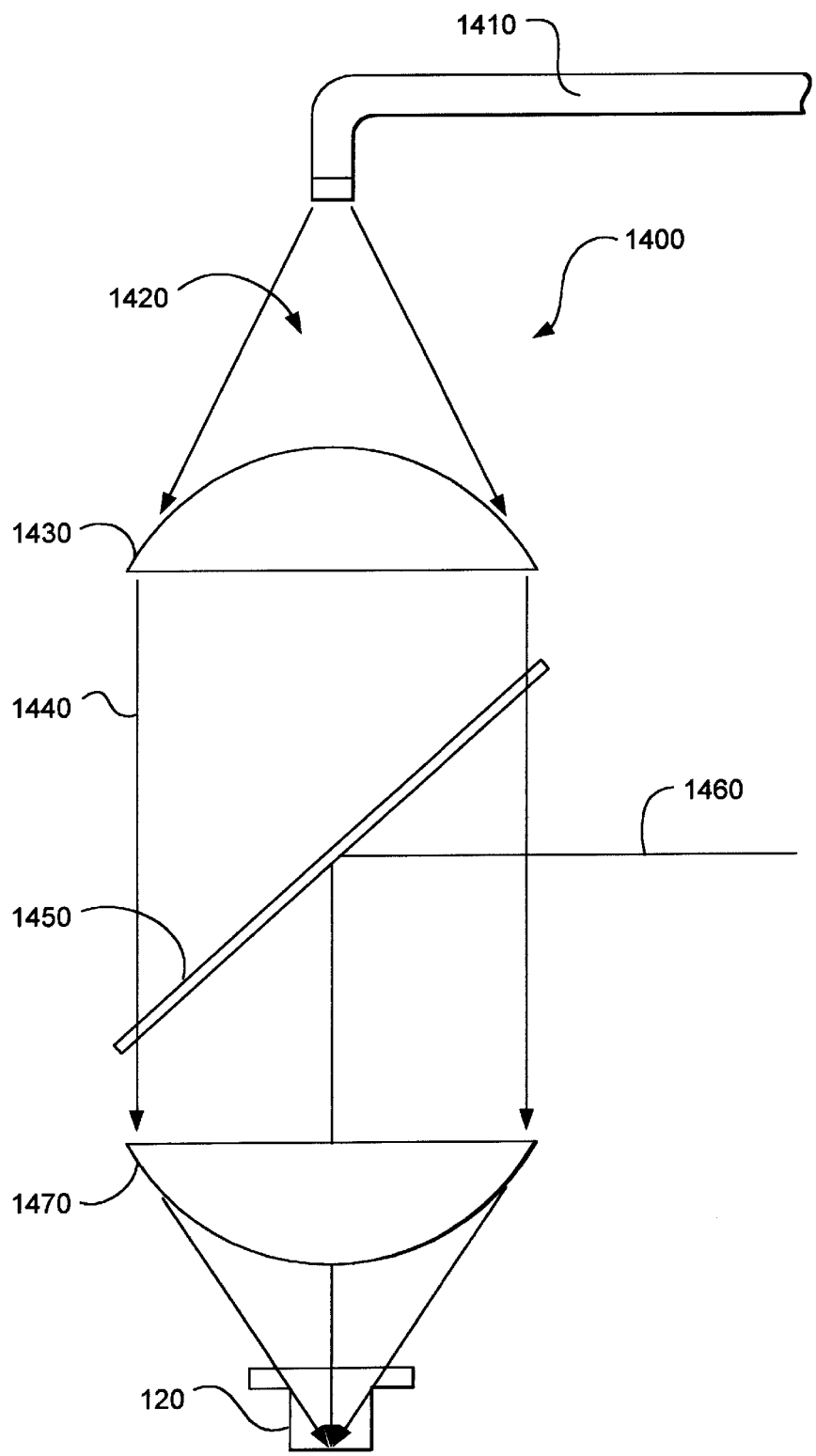
FIG. 14 illustrates a schematic diagram of a combined illumination light/laser beam delivery system, representing an embodiment of the invention.

It can be appreciated from FIG. 13 that there are no pins, or other structures, that project above the top surface of the vacuum chuck 140. This permits the glass slide 130 to be moved in any direction parallel with the top surface without constraint Turning now to FIG. 14, a very high numerical aperture illuminator 1400 for an LCM device is depicted. The illuminator 1400 provides a large working distance. A fiber optic 1410 provides a source of white light illumination. The diverging beam 1420 from the fiber optic 1410 can have a numerical aperture of approximately 0.4. A collimator lens 1430 collimates the light from the fiber optic 1410. The collimator lens 1430 can be an aspheric lens (e.g., a Melles Griot (01 LAG 025) aspheric-like lens). A collimated beam 1440 from the collimator lens 1430 then passes though a beam splitter 1450. The beam splitter 1450 permits the injection of a laser beam 1460. After reflection by the beam splitter 1450, the laser beam 1460 is coaxial with the white light illumination. Both types of light then reach a condenser lens 1470. Condenser lens 1470 can be a Melles Griot (01 LAG 010) or (01 LAG 010) or other similar aspheric-like lens. The condensed coaxial beams are then incident upon and pass through the microcentrifuge tube cap 120. The focusing beam that results from the condenser lens 1470 can have a numerical aperture of approximately 0.8. This can be characterized as a focusing beam. The microcentrifuge tube cap 120 is located on top of a slide with cells to be sampled (not shown).

Figure 15:
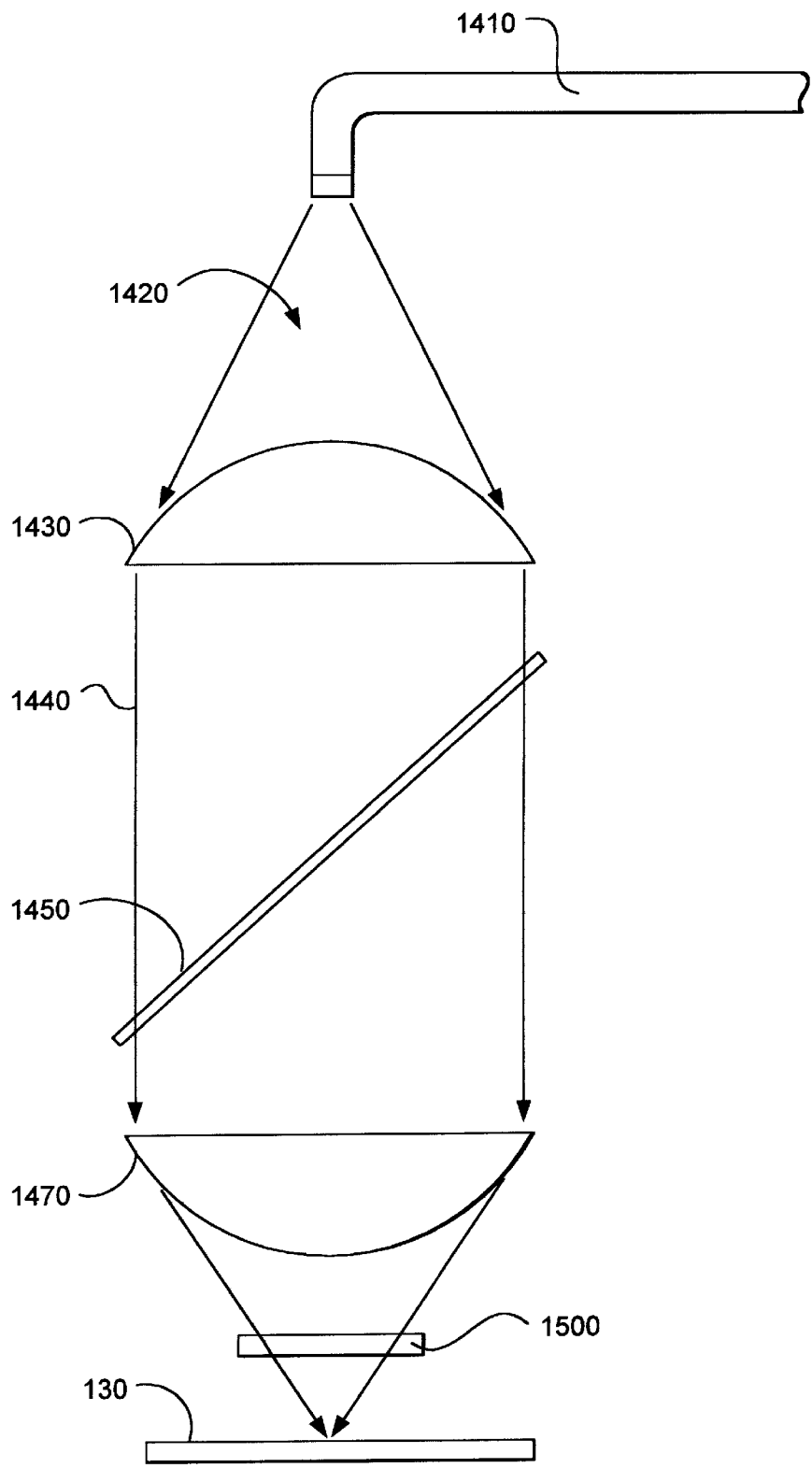
FIG. 15 illustrates a schematic view of a combined illumination/laser beam delivery system with a diffuser in place, representing an embodiment of the invention.

Turning now to FIG. 15, another embodiment of the high numerical aperture illuminator is depicted. In this embodiment, a diffuser 1500 is located beneath the condenser lens 1470 at above the glass slide 130 that contains the cells to be sampled.

More generally, any suitable scattering media can be used to provide the functions of the diffuser 1500. Providing such a scattering media near the tissue to scatter the light results in dramatically improved illumination of the sample and much better visualization. A scattering media of this type eliminates the need for refractive index matching of the sample. Such a scattering media can allow visualization of the cell nucleus and other subcellular structures that would normally be obscured by normal illumination techniques.

The scattering media can be a diffuser material. A diffuser material that is suitable for use as the scattering media is milk or opal glass which is a very dense, fine diffuser material. For instance, a suitable milk glass is available from Edmund Scientific as Part No. P43,717. Standard laser printer/photocopier paper can even be used as the scattering media. Other types of transparent scattering media can be used, such as, for example, frosted glass, a lenticular sheet, a volume diffuser, and/or a surface diffuser. In any event, the scattering media should be a material that aggressively scatters the illumination light. A single sheet of typical ground glass is generally inadequate and needs to be combined in multiple layers as a serial stack of three or four sheets of ground glass to diffuse the illumination light sufficiently.

Figure 16:
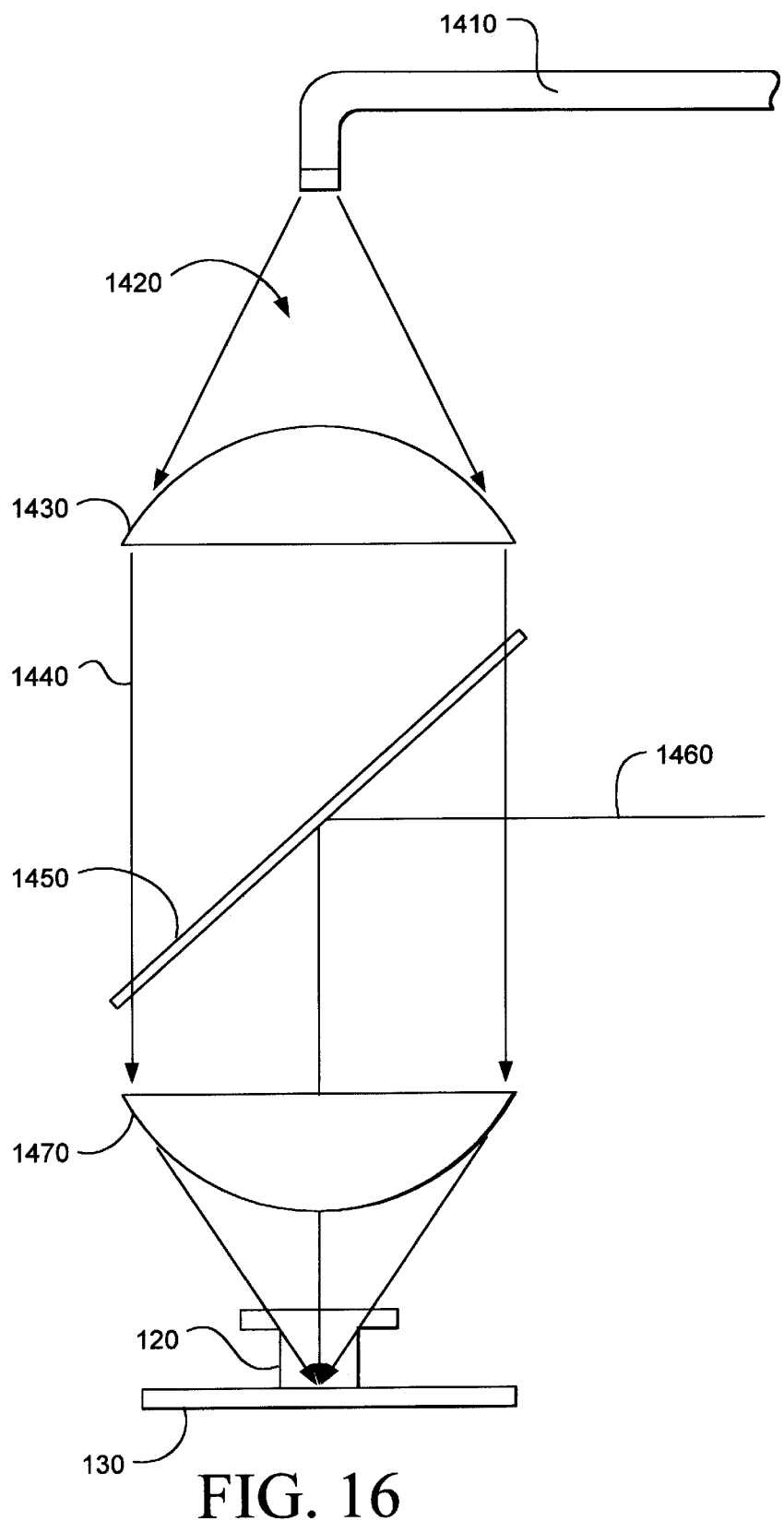
FIG. 16 illustrates a schematic view of a combined illumination/laser beam delivery system with a cap in place, representing an embodiment of the invention.

Turning now to FIG. 16, after the diffuser 1500 is replaced with a microcentrifuge tube cap 120, the desired cells can be located using the image acquired during the step represented in FIG. 15. Then, the laser beam 1460 can be introduced, reflected off the beam splitter 1450 and directed into the microcentrifuge tube cap 120 so as to acquire the desired sample.

The purpose of the illuminator design is to provide a very high numerical aperture illuminator for an LCM device. Such an LCM device requires a large working distance. While an illuminator that uses a 40× objective with 0.8 numerical aperture may seem to give better visualization, this design has problems since the working distance for the 40× objective is very small, (e.g., less than 1 millimeter). Thus it is critical for a design that uses a thick dome carrier to have an illumination design with a much longer working distance. A thick dome carrier is a sample carrier whose top and bottom are spaced apart more than a small distance. This is important because the sample is adjacent the bottom of the sample carrier and the objective cannot move closer to the sample than the top of the sample carrier.

The focusing lens 190 can be replaced with a Melles Griot aspheric condenser lens such as a 01 LAG 010. Such a lens has a numerical aperture of about 0.75 and a working distance of about 25 millimeters. Such a lens is not corrected for chromatic aberrations like the 40× objective. Experiments done using a spherical lens as a condenser gave good improvement in visualization. This spherical lens clearly did not have the corrections for aberrations that are built into the 40× objective.

The laser beam can be focused through this condenser lens like the focusing lens 190. This condenser lens has roughly one-half the focal length of the current lens so the laser beam will be focused down to roughly 15 microns.

In an alternative embodiment the design could use a compound lens like the lens in a barcode scanner. Such a compound lens would have a central region for the laser and a surrounding region that would act as a high numerical aperture with regard to the white light illumination.

Figure 17:
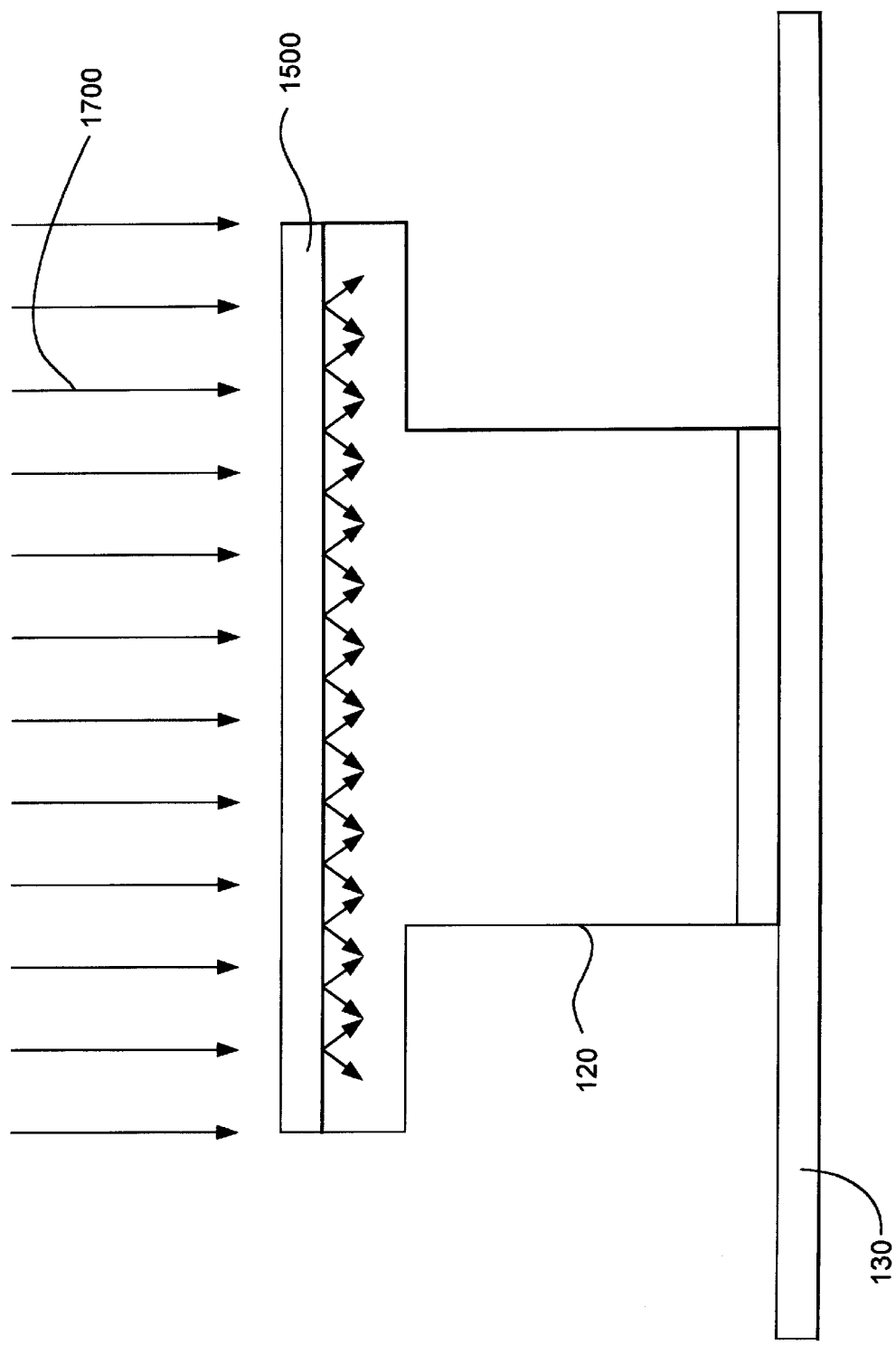
FIG. 17 illustrates a schematic view of an integrated cap/diffuser, representing an embodiment of the invention.

Turning now to FIG. 17, in one embodiment the diffuser 1500 can be located adjacent to the microcentrifuge tube cap 120. In this embodiment the microcentrifuge tube cap 120 is located just above the glass slide 130. Collimated light 1700 is incident upon the diffuser 1500. The diffuser 1500 causes the collimated light to enter into and pass through the cap at an infinite variety of angles. In this way, shadows are reduced and the quality of the imagery is improved.

The diffuser 1500 can be a volumetric diffuser or a surface diffuser. In the case of a volumetric diffuser, the diffuser 1500 can be frosted glass, a speckle based holographic diffuser or even a piece of paper. In the case of a surface diffuser, the diffuser 1500 can be a lenticular sheet, a speckle based holographic surface diffuser or any other suitable topological surface.

Figure 18:
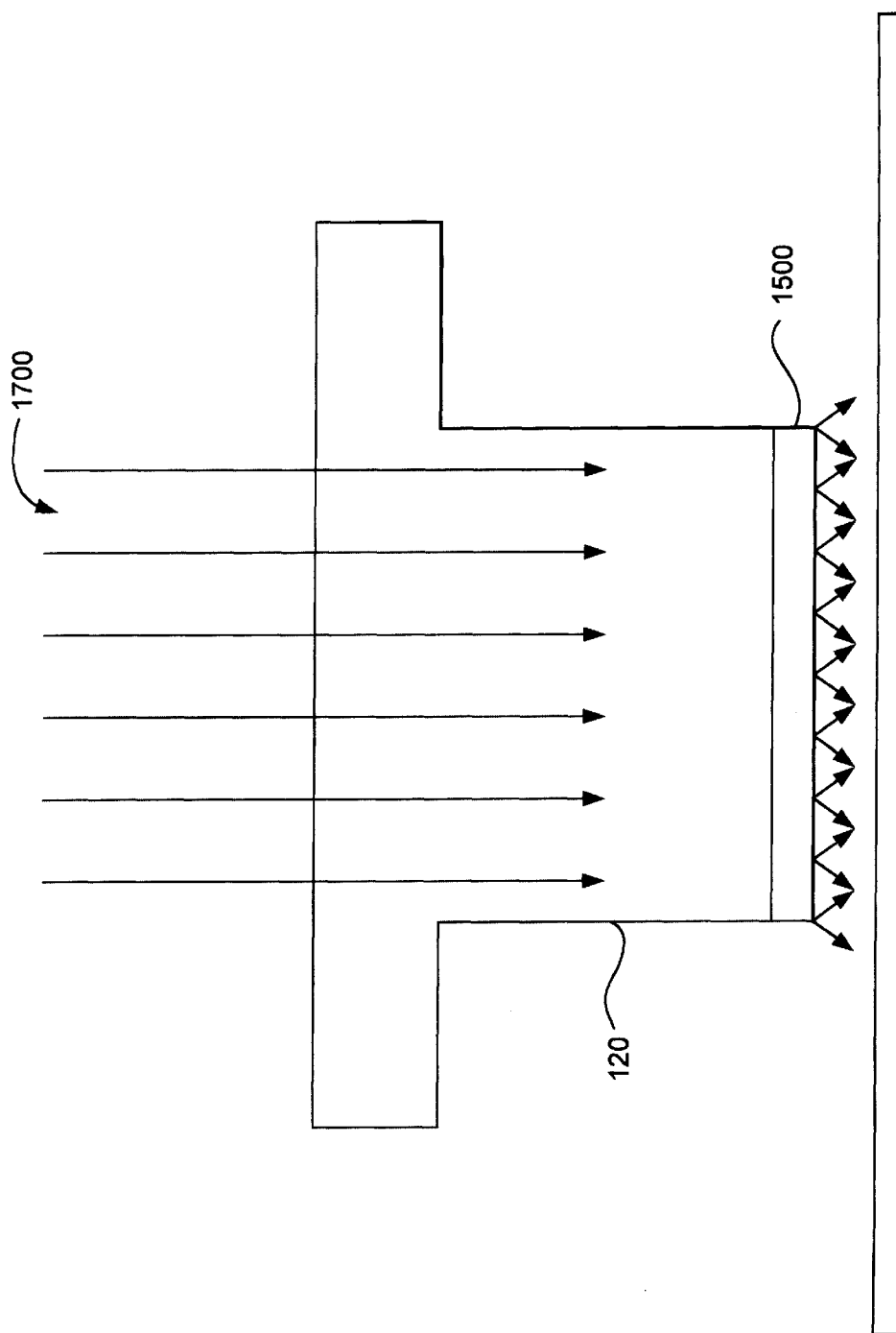
FIG. 18 illustrates a schematic view of an integrated cap/diffuser, representing an embodiment of the invention.

Turning now to FIG. 18, the diffuser 1500 in this embodiment is located adjacent to the bottom of the microcentrifuge tube cap 120. The collimated light 1700 passes through the microcentrifuge tube cap 120 and is incident upon the diffuser 1500. As the previously collimated light emerges from the diffuser 1500 it is scattered into a wide range of angles. In this embodiment, the diffuser 1500 is spaced apart from the glass slide 130.

The scattering media (e.g., diffuser 1500) can be directly or indirectly connected to the transfer film carrier and/or the LCM transfer film. Alternatively, the scattering media can be formed on a surface of, or the interior of, the transfer film carrier and/or the LCM transfer film. The scattering media can be fabricated so as to shape the LCM beam and/or the illumination beam. The scattering media needs to be within a few millimeters of the sample to be effective. A few millimeters means less than one centimeter, preferably less than five millimeters.

The process of operating the instrument begins by visualizing the tissue from which the sample is to be acquired. The tissue is then moved to bring the portion that is to be acquired directly below the principal axis of the instrument. A laser capture microdissection transfer film is then set over the desired area. In a preferred embodiment the film is spaced to within a few microns of the top surface of the sample. Alternatively, the film can be placed in contact with the top of the sample with a pressure sufficient to allow transfer without forcing nonspecific transfer. Finally, the laser is pulsed to heat the film and remove the tissue. The film needs to be pulled off of the sample quickly. Though the velocity should be such that the sample is thixotropically sheared.

Practical Applications of the Invention

A practical application of the invention that has value within the technological arts is the collection of a large database of gene expression patterns of both healthy and diseased tissue, at different stages of diseases. This database will be used to more fully understand that pathogenesis of cancer and infectious diseases. The invention will enable a scientist to identify gene patterns and incorporate this information into effective diagnostics for disease. The invention will allow medical doctors to compare actual patient tissue samples with archived data from patient samples at different disease stages, thereby allowing them to prescribe more effective stage therapies, eliminate unnecessary procedures, and reduce patient suffering. Other research areas where the invention will find use are drug discovery, developmental biology, forensics, botany, and the study of infectious diseases such a drug-resistant tuberculosis. There are virtually innumerable uses for the invention, all of which need not be detailed here.

Advantages of the Invention

A laser capture microdissection instrument and/or method representing an embodiment of the invention can be cost effective and advantageous for at least the following reasons. The invention will replace current methods with better technology that allows for more accurate and reproducible results. The invention can be used to provide a low cost injection molded polymer disposable that integrates a laser capture microdissection transfer film into the interior surface of an analysis container such as a microcentrifuge tube (e.g., an EPPENDORF™ tube).

All publications, patent applications, and issued patents mentioned in this application are hereby incorporated herein by reference in their entirety to the same extent as if each individual publication, application, or patent was specifically and individually indicated to be incorporated in its entirety by reference.

All the disclosed embodiments of the invention described herein can be realized and practiced without undue experimentation. Although the best mode of carrying out the invention contemplated by the inventors is disclosed above, practice of the invention is not limited thereto. It will be manifest that various additions, modifications and rearrangements of the features of the invention may be made without deviating from the spirit and scope of the underlying inventive concept. Accordingly, it will be appreciated by those skilled in the art that the invention may be practiced otherwise than as specifically described herein.

For example, the individual components need not be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable materials. Further, although the LCM instrument disclosed herein is described as a physically separate module, it will be manifest that the LCM instrument may be integrated into other apparatus with which it is associated. Furthermore, all the disclosed elements and features of each disclosed embodiment can be combined with, or substituted for, the disclosed elements and features of every other disclosed embodiment except where such elements or features are mutually exclusive.

It will be manifest that various additions, modifications and rearrangements of the features of the invention may be made without deviating from the spirit and scope of the underlying inventive concept. It is intended that the scope of the invention as defined by the appended claims and their equivalents cover all such additions, modifications, and rearrangements. The appended claims are not to be interpreted as including means-plus-function limitations, unless such a limitation is explicitly recited in a given claim using the phrase "means-for." Expedient embodiments of the invention are differentiated by the appended subclaims.

What is claimed is:

1. A laser capture microdissection method, comprising:

providing a sample that is to undergo laser capture microdissection;

positioning said sample within an optical axis of a laser capture microdissection instrument;

providing a transfer film carrier removably positioned in a transfer film carrier handling subsystem, said transfer film carrier having a substrate surface and a laser capture microdissection transfer film coupled to said substrate surface; and then placing said laser capture microdissection transfer film in juxtaposition with said sample by moving said transfer film carrier handling subsystem, said laser capture microdissection transfer film being placed in juxtaposition with a pressure sufficient to allow laser capture microdissection transfer of a portion of said sample to said laser capture microdissection transfer film, without forcing nonspecific transfer of a remainder of said sample to said laser capture microdissection film; and then transferring a portion of said sample to said laser capture microdissection transfer film, without forcing nonspecific transfer of a remainder of said sample to said laser capture microdissection transfer film, wherein transferring includes
moving said laser capture microdissection transfer film and said portion of said sample away from said remainder of said sample with said transfer film carrier handling subsystem, wherein placing includes
swinging said transfer film carrier handling subsystem toward said optical axis; and then
lowering both said transfer film carrier and said transfer film carrier handling subsystem toward said sample along a direction substantially parallel to said axis, and wherein lowering includes
contacting said sample with said laser capture microdissection transfer film; and then
contacting said transfer film carrier with a weight as to exert said pressure, wherein contacting said sample with said laser capture microdissection transfer film includes
retarding vertical motion of said transfer film carrier handling subsystem and
lowering said transfer film carrier at a reproducible rate so that said transfer film carrier undergoes a self-leveling step; and contacting said transfer film carrier with said weight includes
retarding vertical motion of the transfer film carrier handling subsystem; and
lowering said weight at approximately said reproducible rate so that said weight undergoes a self-leveling step.

2. The laser capture microdissection method of claim 1, wherein transferring includes
raising both said transfer film carrier and said transfer film carrier handling subsystem away from said remainder of said sample along a direction substantially parallel to an axis; and then
swinging said transfer film carrier handling subsystem away from said optical axis.

3. The laser capture microdissection method of claim 2, wherein raising includes
lifting a weight away from said transfer film carrier so as to reduce said pressure; and then
lifting said transfer film carrier and said laser capture microdissection transfer film away from said remainder of said sample.

4. A laser capture microdissection method, comprising:

providing a sample that is to undergo laser capture microdissection;

positioning said sample within an optical axis of a laser capture microdissection instrument;

providing a transfer film carrier removably positioned in a transfer film carrier handling subsystem, said transfer film carrier having a substrate surface and a laser capture microdissection transfer film coupled to said substrate surface; and then placing said laser capture microdissection transfer film in juxtaposition with said sample by moving said transfer film carrier handling subsystem, said laser capture microdissection transfer film being placed in juxtaposition with a pressure sufficient to allow laser capture microdissection transfer of a portion of said sample to said laser capture microdissection transfer film without forcing nonspecific transfer of a remainder of said sample to said laser capture microdissection film; and then transferring a portion of said sample to said laser capture microdissection transfer film, without forcing nonspecific transfer of a remainder of said sample to said laser capture microdissection transfer film, wherein transferring includes moving said laser capture microdissection transfer film and said portion of said sample away from said remainder of said sample with said transfer film carrier handling subsystem, wherein transferring includes
raising both said transfer film carrier and said transfer film carrier handling subsystem away from said remainder of said sample along a direction substantially parallel to an axis; and then
swinging said transfer film carrier handling subsystem away from said optical axis, wherein, raising includes
lifting a weight away from said transfer film carrier so as to reduce said pressure; and then, lifting said transfer film carrier and said laser capture microdissection transfer film away from said remainder of said sample
wherein lifting said weight away from said transfer film carrier includes:
  retarding vertical motion of said transfer film carrier handling subsystem; and
  raising said weight away from said transfer film carrier at a reproducible rate and
lifting said transfer film carrier and said laser capture microdissection transfer film away from said remainder of said sample includes:
  retarding vertical motion of said transfer film carrier handling subsystem: and
  raising said transfer film carrier and said laser capture microdissection transfer film away from said remainder of said sample so that said portion of said sample is thixotropically sheared away from said remainder of said sample.

5. The laser capture microdissection method of claim 4, further comprising, before providing a transfer film carrier removably positioned in a transfer film carrier handling subsystem,
  swinging said transfer film carrier handling subsystem to a load position.

\* \* \* \* \*